United States Patent [19]
Colman et al.

US005770693A

[11] Patent Number: 5,770,693
[45] Date of Patent: Jun. 23, 1998

[54] CALPAIN-INHIBITING PEPTIDE ANALOGS OF THE KININOGEN HEAVY CHAIN

[75] Inventors: Robert W. Colman, Moylan, Pa.;
Harlan N. Bradford, Lindenwold, N.J.;
Bradford A. Jameson, Philadelphia, Pa.

[73] Assignee: Temple University-Of The Commonwealth System of Higher Education, Philadelphia, Pa.

[21] Appl. No.: 468,858

[22] Filed: Jun. 6, 1995

Related U.S. Application Data

[62] Division of Ser. No. 385,391, Feb. 7, 1995, Pat. No. 5,663,294, which is a continuation of Ser. No. 109,854, Aug. 20, 1993, abandoned, which is a continuation of Ser. No. 719,051, Jun. 21, 1991, abandoned.

[51] Int. Cl.⁶ .......................... A61K 38/00; A61K 38/02; C07K 5/00; C07K 7/00
[52] U.S. Cl. ........................... 530/333; 514/13; 514/12; 530/324; 530/326
[58] Field of Search ....................... 514/13, 12; 530/326, 530/325, 324, 333

[56] References Cited

FOREIGN PATENT DOCUMENTS 0 395 309  10/1991  European Pat. Off. .

OTHER PUBLICATIONS

Salvesen et al., *Biochem J.* 234, 429–434 (1986).
Muller–Esterl, *Atemw. Lungenkrkh. Jahrgang 14*, 1. Supp. Heft S11–S22 (1988).
Teno et al., *Int. J. Peptide Protein Res.*, 30, 93–98 (1987).
Matsueda et al., *Chem. Lett.* 191–194 (Feb. 1990).
Puri et al., *Trans. Assoc. Amer. Physicians*, vol. CII, 13–19 (1989).
Ishiguru et al., *Biochemistry*, vol. 26, No. 28, 7021–7029 (1987).
Bradford et al., *Biochemical Journal*, vol. 270, No. 1, 83–90 (1990).
Higashiyama et al., *Biochemistry*, vol. 25, 1669–1675 (1986).

*Primary Examiner*—Avis M. Davenport
*Attorney, Agent, or Firm*—Seidel, Gonda, Lavorgna & Monaco, PC

[57] ABSTRACT

Synthetic peptide analogs of human kininogen are provided which are conformationally restricted by means of intramolecular bonding. The peptides mimic the biological activity of human kininogen by inhibiting the activity of the biologically significant protease, calpain. The peptides are designed by means of an equilibrium conformational model of the kininogen heavy chain.

16 Claims, 1 Drawing Sheet

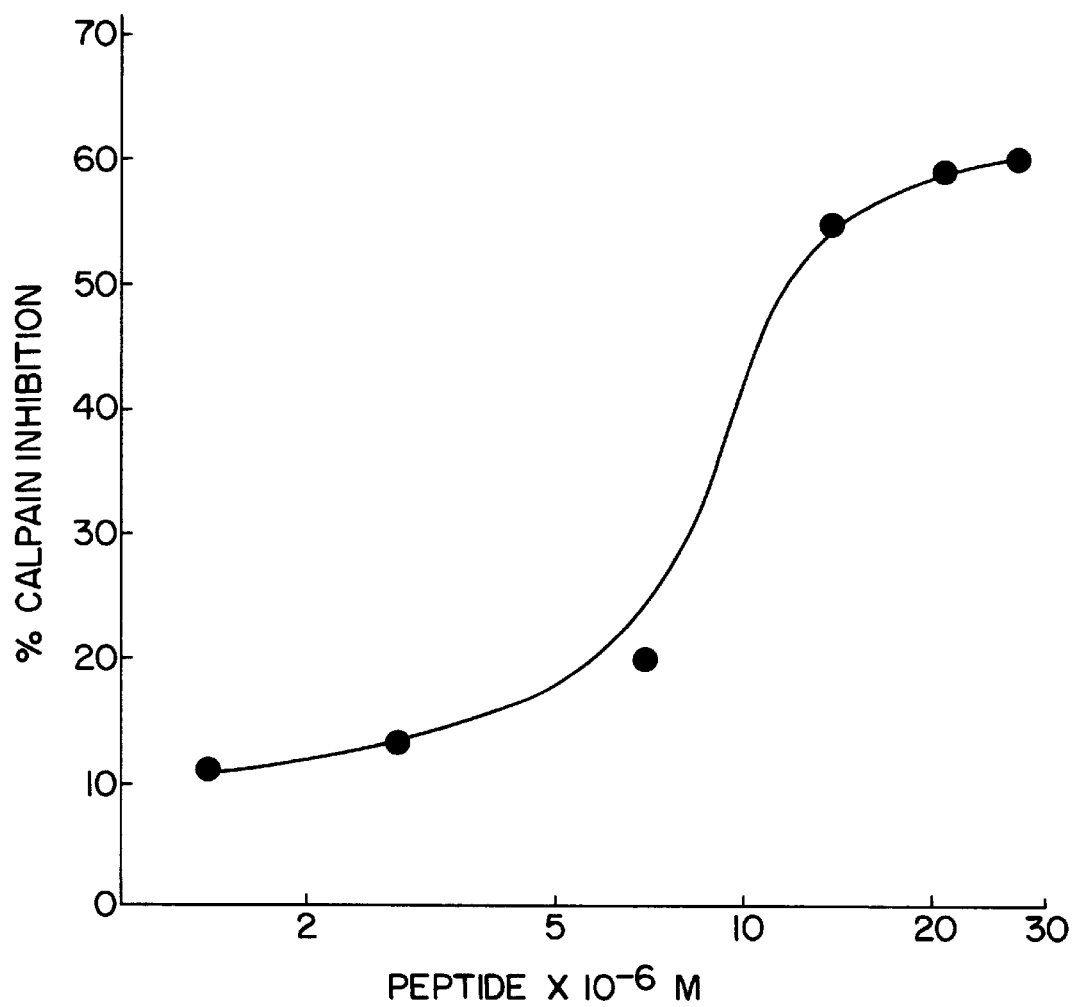

CALPAIN-INHIBITING PEPTIDE ANALOGS OF THE KININOGEN HEAVY CHAIN

CROSS REFERENCE TO RELATED APPLICATION

This is a divisional of application Ser. No. 08/385,391 filed Feb. 7, 1995, now U.S. Pat. No. 5,663,294 which is a continuation of application Ser. No. 08/109,854 filed on Aug. 20, 1993, abandoned, which is a continuation of application Ser. No. 07/719,051 filed on Jun. 21, 1991, abandoned.

REFERENCE TO GOVERNMENT GRANT

The invention described herein was supported in part by National Institutes of Health grant HL 24365.

FIELD OF THE INVENTION

The invention relates to synthetic peptide analogs of the human plasma proteins, high and low molecular weight kininogen.

BACKGROUND OF THE INVENTION

Activation and aggregation of human platelets leads to the formation of blood clots (thrombi). It is well established that the binding of fibrinogen to specific receptors on platelets is essential for platelet aggregation. Unstimulated platelets do not bind fibrinogen and do not aggregate during circulation. When platelets are stimulated by certain physiological agonists, such as ADP, thrombin, etc., the fibrinogen receptors associated with the glycoprotein IIb/IIIa complex on the platelet become exposed, resulting in fibrinogen binding leading to platelet aggregation.

Aggregin ($M_r$=100 kDa) is a putative ADP-receptor on the platelet surface. It has been shown to be completely cleaved during thrombin- and plasmin-induced platelet aggregation. The binding of thrombin and plasmin to their receptors on the platelet surface is a important requirement for these plasma proteases to elicit aggregin proteolysis and platelet aggregation.

Thrombin- and plasmin-induced platelet aggregation and cleavage of aggregin are indirectly mediated by intracellularly activated calpain expressed on the platelet surface. Thrombin- and plasmin-induced platelet aggregation are inhibited by cysteine protease inhibitors, including kininogens.

Kininogens exist in human plasma in two molecular forms, high molecular weight kininogen (HK) and low molecular weight kininogen (LK). HK is synthesized in the liver as a single chain and secreted into plasma at a concentration of 0.67 $\mu$M. HK is cleaved by plasma kallikrein, resulting in the formation of (i) a 64 kDa heavy chain and a 56 kDa light chain linked by a single disulfide bond, and (ii) the nonapeptide bradykinin. The latter has multiple inflammatory effects including induction of pain, vasodilation and increased vascular permeability (Colman, *J. Clin. Invest.* 73, 1249–1253 (1984)). Studies of human mutants (e.g., Colman et al., *J. Clin. Invest.* 56, 1650–1662 (1975)) delineated the coagulant function of HK. LK, present in plasma at 2.4 $\mu$M, releases bradykinin preferentially after exposure to tissue kallikrein, and does not exhibit coagulant activity. LK contains a short light chain of 4 kDa, and has a total molecular weight of 66 kDa, in contrast to the 56 kDa light chain and 120 kDa total weight of intact HK. Both HK and LK have an identical heavy chain which results from translation of alternately spliced mRNAs from a single gene.

The major function of the heavy chain of HK and LK is to inhibit proteases with cysteine at their active sites. Such cysteine proteases include the calcium-activated cysteine proteases, more commonly known as "cal-pains" (Schmaier et al., *J. Clin. Invest.* 77, 1565–1573 (1986)). The kininogen heavy chain contains three repeating units or "domains" having mutual sequence homology, designated D1, D2, and D3. The domains are derived evolutionarily from the more primitive stefins and cystatins by gene duplication. The crystal structure of chicken egg white cystatin has been solved by Bode et al., *EMBO J.*, 7, 2593–2599 (1988).

Of the three kininogen heavy chain repeats, D2 and D3 contain the pentapeptide Gln-Val-Val-Ala-Gly ("QVVAG"). Although both D2 and D3 contain the QVVAG sequence and are inhibitors of cysteine proteinases, only D2 is effective in inhibiting calpain (Salvesen et al., *Biochem. J.* 234, 429–434 (1986); Muller-Esterl, *Atemw.-Lungenkrkh. Jahrgang* 14, 1. Suppl.-Heft S11S–S22 (1988). Teno et al., *Int. J. Peptide Protein Res.* 30, 93–98 (1987) report weak activity of the QVVAG pentapeptide in inhibiting the thiol protease papain.

Reocclusion of coronary arteries is a frequent complication following thrombolytic therapy. It has been postulated that reocclusion is due to plasmin-induced activation of platelets. High concentrations of plasmin, such as might occur in therapeutic thrombolysis, are known to cause platelet aggregation.

Coronary artery restenosis following angioplasty has been linked to platelet activation by protease agonists. Restenosis may be initiated by thrombin-stimulated release of growth factors from platelets.

What is needed is a method of inhibiting stimulation and aggregation of platelets by protease agonists, specifically a method of inhibiting stimulation of platelets by inhibiting the action of platelet calpain in facilitating thrombin- and plasmin-induced platelet aggregation.

SUMMARY OF THE INVENTION

A synthetic peptide is provided comprising an amino acid sequence corresponding to a portion of domain 2 of the human kininogen heavy chain. The peptide has a restricted conformation and the ability to inhibit the enzymatic activity of calpain.

In another embodiment, the invention is directed to a method of designing a peptide analog to the kininogen heavy chain domain. The distance between two parts of a molecular model of the kininogen heavy chain domain 2 is determined at conformational equilibrium. The primary structure of the domain is then modified to restrict that distance to the determined distance. A peptide comprising the modified primary structure is then synthesized.

In yet another embodiment of the invention, a method of producing a peptide having a restricted conformation is provided. Accordingly, a peptide having an amino acid sequence corresponding to a portion of the human kininogen heavy chain domain 2 is provided. The conformational equilibrium of a portion of that domain is determined. A covalent modification is introduced into the peptide to restrict a distance between two parts of the peptide to a distance between corresponding parts of the peptide in the equilibrium conformation determined.

The invention further provides pharmaceutical compositions comprising one or more of the peptides in combination with a pharmaceutically acceptable carrier. The activity of platelet calpain is inhibited by the peptides of the invention. Inhibition of platelet calpain results in the inhibition of thrombin- or plasmin-induced platelet aggregation of human platelets incubated with calpain-inhibiting agents.

By "human kininogen heavy chain" is meant the about 64 kDa polypeptide chain, common to both high molecular weight and low molecular weight human kininogen, which polypeptide is obtainable by kallikrein cleavage of high about 120 kDa major kallikrein cleavage fragment and isolation of the about 64 kDa single polypeptide chain therefrom.

By "domain 2" of human kininogen heavy chain is meant the region of the intact 64 kDa polypeptide chain comprising from about amino acid 124 to about amino acid 243 of the mature polypeptide. The mature polypeptide is generated by a post-translational modification which cleaves an 18-amino acid leader from the translated poly-peptide.

DESCRIPTION OF THE FIGURES

FIG. 1 is a plot of calpain inhibition by the following peptide, (SEQ ID NO: 1)

| Cys | Thr | Asp | Asn | Ala | Tyr | Ile | Asp | Ile | Gln |
|-----|-----|-----|-----|-----|-----|-----|-----|-----|-----|
|     |     |     |     | 5   |     |     |     |     | 10  |
| Leu | Arg | Ile | Ala | Ser | Phe | Ser | Gln | Asn | Cys |
|     |     |     |     | 15  |     |     |     |     | 20  | which peptide corresponds to human kininogen heavy chain amino acids 229 through 248, with an intramolecular disulfide bond connecting the cysteine residues.

DETAILED DESCRIPTION OF THE INVENTION

We have found that there is a specific site in the kininogen heavy chain, in addition to the QVVAG sequence, which is a binding or inhibitory site involved in calpain inhibition. The site lies within domain 2. The deduction of the structure of domain 2 was accomplished a homology-based molecular modeling technique reviewed by Jameson in *Nature*, 341, 465–466 (1989), based upon the published structure of cystatin (Bode et al., *Embo J.* 7, 2593–2599 (1988)). Cystatin, like kininogen, is a cysteine protease inhibitor. The modeled domain 2 structure is used as a design template for synthesizing peptides according to the present invention that are expected to adopt a conformational repertoire overlapping that of the native protein. The sequences identified herein from the kininogen heavy chain have not been previously identified as being inhibitory for cysteine proteases.

The calpain-inhibiting peptides of the invention are believed capable of selectively inhibiting platelet activation by thrombin and/or plasmin. Other peptides, such as the RGD-containing proteases, may inhibit platelet aggregation in response to cell agonists, but may also lead to prolonged bleeding times and hemorrhagic complications.

The primary structure of the kininogen heavy chain is known (Salveson et al., *Biochem. J.* 234, 429–434 (1986), incorporated herein by reference; Kellerman et al., *J. Biochem.* 154, 471–478 (1986)) incorporated herein by reference). While the significance of the QVVAG sequence as a weak inhibitor of papain is known (Tenno et al., *Int. J. Peptide Protein Res.* 30, 93–98 (1987)), the prior art attaches no functional significance to any other sequence as a potential inhibitor of calpain.

Traditional syntheses of the linear amino acid sequence of biologically interesting proteins may result in peptides that are either biologically inactive or, at best, marginally active. We have created a molecular model of the three-dimensional structure of heavy chain domain 2. The structure created in this manner is used as a template for designing conformationally-restricted synthetic analogs having calpain inhibiting activity. Using both distance and geometric constraints imparted through measurements of the subdomains within the calculated structure, constraints are artificially introduced, e.g., disulfide bonds, to limit the conformational freedom of a synthetic peptide that incorporates the relevant amino acids. One particular conformationally-restricted synthetic peptide analog having potent calpain inhibiting activity corresponds to kininogen heavy chain residues 211–230, according to the numbering of the amino acids of the mature polypeptide. The model disclosed herein may be utilized to prepare additional conformationally-restricted synthetic peptides having similar activity.

Appendix 1 hereto contains the set of Brookhaven coordinates and connect statement specifying our equilibrium conformation model of the major portion of kininogen heavy chain domain 2 comprising the 109 amino acids spanning positions 124 to 232, inclusive. The corresponding graphic molecular model satisfying these coordinates may be generated by inputting the coordinates and connect statement into any of the many commercially available molecular modeling programs which are capable of reading files in the Brookhaven format. Such programs include, for example, those of BioDesign, Inc., Pasadena, Calif.; Biosym Technologies, San Diego, Calif.; Tripos, St. Louis, Mo.; Polygen, Waltham, Ma.; and Chemical Design Ltd., Oxford, UK. The data may be entered as an ASCII file.

According to the Brookhaven format shown in the Appendix, each of the atoms of kininogen heavy chain residues 124–232 is assigned a number and respective X, Y and Z coordinates. The coordinate portion of the listing begins with the cysteine residue (CYS 1) at position 124 of the mature kininogen heavy chain. The atom types are identified as "N" for nitrogen, "HN" for hydrogen which is connected to a nitrogen atom, "C" for carbon, "CA" for α carbon, "CB" for β carbon, "CG" for γ carbon, and so forth. Identical atoms of branched side chains are indicated by numbers. Thus, the two γ carbons of VAL 5 are designated "CG 1" and "CG 2" respectively.

The data file further comprises a connect statement which begins immediately after the coordinates for atom 1068. The connect statement identifies the covalent bonding pattern of each of the 1068 atoms. Thus, for example, the 10th entry of the connect statement (CONNECT 10) indicates that atom 10, which is the nitrogen atom of LEU 2 (corresponding to amino acid 125 of the mature kininogen heavy chain sequence), is bonded to atom 12 (the α carbon of the same residue), atom 6 (the carbonyl carbon of the neighboring cysteine residue), and atom 11 (hydrogen). The complete data file of 1,068 coordinates, together with the connect statement for these entries, specifies the equilibrium conformation of kininogen heavy chain domain 2.

The analogs of the invention generally have an amino acid sequence similar to the native domain 2 sequence. However, a covalent modification is introduced to restrict the analog to the conformation (or one close to it) displayed by the above model. Generally, this is accomplished by determining a distance between two non-contiguous parts of the amino acid chain according to the model. Then a chemical moiety is introduced to fix that determined distance in the analog. For example, a 5–6Å distance can be fixed using a disulfide bond. Cysteine residues can be introduced at the appropriate positions in the model and then the new cysteine-containing model is tested for its ability to mimic the structure observed in the model.

The use of artificially introduced cysteine residues to create a disulfide bridge is one way to conformationally restrict the peptides. Disulfide bonds, however, are intrinsically unstable and it is difficult to obtain a homogeneous solution of intradisulfide-bonded species without concomitant mixed disulfides. The disulfide bridges can be replaced in biologically active peptides by stable covalent bonds. There are several strategies which can be utilized in the covalent closure of the peptides. Two of these strategies are described below.

The peptide can be internally crosslinked via the side chains of a lysine ε-amino group and the carboxylic acid function of a glutamic or aspartic acid side chain, thus creating an amide bond. The peptide is synthesized according to standard procedures on a low substitution (0.2 mM/gm or less) para-methylbenzhydrylamine resin. The first residue added to the resin is an N-α-tBOC,ε-fMOC lysine. The rest of the peptide synthesis is continued normally using tBOC chemistry until the final residue is added. The last residue to be added is a Z-protected glutamic acid, where the carboxylic acid moiety is protected with a tert-butyl group. Treatment of the peptide resin with piperidine/DMF removes the fMOC group from the ε-amino group of the initial lysine without affecting any other protection groups. Subsequent treatment with trifluoracetic acid removes the protection of the carboxylic acid group of the glutamic acid. Following neutralization, the peptide is covalently closed using a standard diimide-meditated coupling reaction. It should be emphasized that this is only one of the ways in which the synthetic peptide can be covalently closed.

Other fMOC/tBOC strategies include covalent closure of the peptide between two free amino groups utilizing toluene-2,4-diisocyanate (TDI), a heterobifunctional cross-linker. The methyl group of the aromatic ring of TDI prevents the isocyanate group in the 2 position from reacting at a pH 7.5 or below, whereas the isocyanate group in the para position is highly reactive. A shift in pH to greater than 9.0 will initiate a reaction with the isocyanate group in the 2 position, thus enabling highly specific and controlled conditions for covalent closure of the peptide. By utilizing a variety of different strategies for restricting the conformation of these peptides, distance geometries and orientation of the folded peptide can be controlled. Any such strategies employing chemical reactions known in the art may be used.

Using these techniques, synthetic peptide analogs can be made and tested for their ability to mimic the biological functions of the parent kininogen molecule, specifically, calpain inhibition.

One particularly useful peptide analog which was derived using the techniques described herein comprises amino acids 211–230 of the kininogen heavy chain. This peptide was restricted conformationally using cysteine-cysteine disulfide bonds, but other restricting means may be advantageously used. Peptide 211–230, crosslinked at cysteine residues 211 and 230, inhibits the activity of calpain, and, as a consequence, may be used to inhibit platelet activation by thrombin and/or plasmin. Methods of assaying calpain inhibition are known in the art. One such method is described hereinafter in Example 2. Another method is described in Example 19 of European Patent Application 393,457 (1990).

The present peptides are relatively short in length and therefore they are easily synthesized by chemical means. Such synthetic peptides have many advantages over the use of the entire kininogen heavy chain, or the entire D2 domain. Large portions of the heavy chain cannot conveniently be made by synthetic techniques and must be made by recombinant DNA techniques, which are expensive and time consuming. Additionally, proteins may present solubility and immunogenicity problems when introduced into a patient. Short synthetic peptides are much more soluble and less immunogenic than larger proteins.

As used herein, "peptide" refers to a linear series of no more than about 50 amino acid residues connected to one another by peptide bonds between the alpha-amino groups and carboxy groups of adjacent amino acid residues. Additional covalent bonds between portions of the peptide are also present to restrain the conformation of the molecule, such as amide and disulfide bonds. When used herein, "protein" refers to a linear series of greater than 50 amino acid residues connected one to the other as in a peptide. The term "synthetic peptide" means a chemically derived chain of amino acid residues linked together by peptide bonds that is free of naturally occurring proteins and fragments thereof.

The three-letter symbols used to represent the amino acid residues in the peptides of the present invention are those symbols commonly used in the art. The amino acid residues are preferred to be in the "L" isomeric form. However, residues in the "D" isomeric form may be substituted for any L-amino acid, as long as the desired functional property of calpain inhibition is retained by the peptide. The three-letter symbols used herein refer to the following amino acids: Ser is serine; Ile is isoleucine; Gln is glutamine; Phe is phenylalanine; His is histidine; Trp is tryptophan; Lys is lysine; Asn is asparagine; Leu is leucine; Gly is glycine; Thr is threonine; Asp is aspartic acid; Arg is arginine; and Ala is alanine.

Peptides of the present invention include any analog, fragment or chemical derivative of the peptides capable of inhibiting calpain. The term "analog" refers to any peptide having a substantially identical amino acid sequence to the peptides of the invention in which one or more amino acids have been substituted with other amino acids; the substituted amino acids allow or require the peptide to assume the equilibrium conformation of the domain of the parent protein. Often, cysteine, lysine and glutamic acid will be used for their side chains which can form covalent linkages to restrict the conformation of a peptide. In addition, conservative amino acid changes may be made which do not alter the biological function of the peptide. For instance, one polar amino acid, such as glycine, may be substituted for another polar amino acid; or one acidic amino acid, such as aspartic acid may be substituted for another acidic amino acid, such as glutamic acid; or a basic amino acid, such as lysine, arginine or histidine may be substituted for another basic amino acid; or a non-polar amino acid, such as alanine, leucine or isoleucine may be substituted for another non-polar amino acid.

The term "analog" shall also include any peptide which has one or more amino acids deleted from or added to an amino acid sequence of kininogen heavy chain domain 2, but which still retains a substantial amino acid sequence homology to kininogen, as well as kininogen's calpain inhibiting activity. A substantial sequence homology is any homology greater than 50% but preferably greater than 90%. The term "fragment" shall refer to any shorter version of the peptides identified herein having at least five amino acid residues, wherein the fragment is capable of inhibiting calpain.

The peptides of the present invention may be prepared by any of the following known techniques. Conveniently, the peptides may be prepared using the solid-phase synthetic technique initially described by Merrifield, in *J. Am. Chem. Soc.* 15, 2149–2154 (1963). Other peptide synthesis techniques may be found, for example, in M. Bodanszky et al., *Peptide Synthesis*, John Wiley & Sons, 2d Ed. (1976) as well as in other reference works known to those skilled in the art. A summary of peptide synthesis techniques may be found in J. Stuart and J. D. Young, Solid *Phase Peptide Synthelia*, Pierce Chemical Company, Rockford, Ill. (1984). The synthesis of peptides by solution methods may also be used, as described in *The Proteins*, vol- II, 3d Ed., Neurath, H. et al., Eds., p. 105–237, Academic Press, New York, NY. (1976). Appropriate protective groups for use in such syntheses will be found in the above texts as well as in J. F. W. McOmie, *Protective Groups in Organic Chemistry*, Plenum Press, New York, NY. (1973). Of course, the present peptides may also be prepared by recombinant DNA techniques, although such methods are not preferred because of the need for purification and subsequent chemical modifications to conformationally restrain the peptides.

In general, these synthetic methods involve the sequential addition of one or more amino acid residues or suitably protected amino acid residues to a growing peptide chain. Normally, either the amino or carboxyl group of the first amino acid residue is protected by a suitable, selectively-removable protecting group. A different, selectively-removable protecting group is utilized for amino acids containing a reactive side group, such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptides of the invention are devoid of benzylated or methylbenzylated amino acids. Such protecting group moieties may be used in the course of synthesis, but they are removed before the peptides are used. Additional reactions may be necessary, as described elsewhere to form intramolecular linkages to restrain conformation.

The peptides of the present invention generally contain at least five amino acid residues and up to fifty amino acid residues, preferably between 6 and 20 amino acid residues. These peptides may be linked to an additional sequence of amino acids either or both at the N-terminus and at the C-terminus, wherein the additional sequences are from 1–100 amino acids in length. Such additional amino acid sequences, or linker sequences, can be conveniently affixed to a detectable label or solid matrix, or carrier. Typical amino acid residues used for linking are tyrosine, cysteine, lysine, glutamic acid and aspartic acid, or the like.

Any peptide of the present invention may be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanolamines (e.g., ethanolamine, diethanolamine and the like).

For use in a method of treatment, such as treatment for inhibiting thrombin- or plasmin-induced platelet aggregation, the synthetic peptides of the present invention may be present in a pharmaceutical composition in admixture with a pharmaceutically-acceptable carrier. The pharmaceutical composition may be compounded according to conventional pharmaceutical formulation techniques. The carrier may take a wide variety of forms depending on the form of preparation desired for administration, e.g., sublingual, rectal, nasal, oral or parenteral. Compositions for oral dosage form may include any of the usual pharmaceutical media, such as, for example, water, oils, alcohols, flavoring agents, preservatives, coloring agents and the like in the case of oral liquid preparations (e.g., suspensions, elixirs and solutions) or carriers such as starches, sugars, diluents, granulating agents, lubricants, binders, disintegrating agents and the like in the case of oral solid preparations (e.g., powders, capsules and tablets). Controlled release forms may also be used. Because of their ease in administration, tablets and capsules represent the most advantageous oral dosage unit form, in which case solid pharmaceutical carriers are obviously employed. If desired, tablets may be sugar coated or enteric coated by standard techniques.

For compositions to be administered parenterally, the carrier will usually comprise sterile water, although other ingredients to aid solubility or for preservation purposes may be included. Injectable suspensions may also be prepared, in which case appropriate liquid carriers, suspending agents and the like may be employed. The parenteral routes of administration may be intravenous injection, intramuscular injection or subcutaneous injection.

For intravenous administration, the peptides may be dissolved in an appropriate intravenous delivery vehicle containing physiologically compatible substances such as sodium chloride, glycine and the like, having a buffered pH compatible with physiologic conditions. Such intravenous delivery vehicles are known to those skilled in the art.

The peptides of the invention may be administered to subjects in any situation where inhibition of calpain activity is desired. Calpain inhibitors may be administered during or after angioplasty or thrombolytic therapy to prevent restenosis or reocclusion. It is believed that restenosis following angioplasty may be initiated by thrombin-stimulated release of growth factors from platelets. Reocclusion, a frequent occurrence after thrombolytic therapy, has been postulated to be caused by plasmin-induced activation of platelets, which is mediated by platelet calpain.

The peptides may be administered by any convenient means which will result in the delivery to the bloodstream of a calpain-inhibiting effective amount. Intravenous administration is presently contemplated as the preferred administration route. The amount administered will depend on the activity of the particular compound administered, which may readily be determined by those of ordinary skill in the art. Generally, the peptides may be administered in an amount sufficient to provide a plasma concentration in the range of from about 10 to about 500 μM, more preferably in the range of from about 50 to about 250 μM. Plasma concentrations higher or lower than these may be utilized, depending upon the activity of the particular compound being administered, and the nature of the treatment.

In addition to inhibition of plasmin- and thrombin-induced platelet aggregation, inhibitors of calpain have other beneficial therapeutic utilities. Abnormal activation of calpain has been linked to diverse disease conditions, such as muscular dystrophy and cataracts. Furthermore, inhibitors of calpain have been shown to be able to limit brain damage caused by the interruption of the supply of blood and oxygen to the brain. Tests with calpain inhibitors in model systems have indicated that inhibition of calpain alone is sufficient to protect brain cells from ischemic damage after ischemic attack. It is contemplated that the peptides of the present invention are useful in any therapeutic circumstance where reduction of calpain activity is desired.

The following non-limiting examples serve to illustrate the practice of the invention.

EXAMPLE 1

This example demonstrates the selection and synthesis of a calpain-inhibiting kininogen analog.

The modeled structure of Appendix 1 was used as a design template in the construction of an analog corresponding to kininogen heavy chain residues 211–230. In order to conformationally restrict the folding equilibria of the resulting synthetic peptide, the cysteine residues at positions 211 and 230 were allowed to form an intrachain disulfide bond in computer-assisted modeling. The predicted folding pattern of the putative structure was tested for its ability to mimic the structure observed in our model of domain 2. Finding satisfactory agreement, the peptide was synthesized according to conventional solid phase procedures. The peptide incorporated the native residues 211–230, with a disulfide residue bond connecting the cysteine residues at positions 211 and 230. The peptide assayed pure upon high performance liquid chromatography. The intrachain disulfide bond was spontaneously formed by diluting the synthesized peptide to a concentration of 100 μg/ml in a solution adjusted to pH 8.5 with $NH_4OH$, followed by stirring open to the atmosphere to ensure oxidation. The resulting disulfide-bonded peptide was then lyophilized.

EXAMPLE 2

This example demonstrates the biological activities of the peptide analogs.

The calpain-inhibiting activity of the disulfide-bonded Example 1 peptide was demonstrated according to a modification of the procedure of Schmaier et al., *J. Clin. Invest.* 77, 1565 (1986). A calpain preparation (5~10 μl) was placed on a floating filter membrane (Marusyk et al., *Anal. Biochem.* 105, 403 (1980)) (Millipore type VMWP) over a buffer containing 50 mM Tris/HCl, pH 7.5 and 2.5 mM EDTA for 45–60 minutes, then carefully removed and used for the following inhibition study. Aliquots (25 μl) of the enzyme (calpain) and buffer or synthetic peptide were added to a cuvette at 25° C. containing 1mM succinyl-Leu-Tyr-amino-4-methylcumarin as the substrate in a buffer consisting of 60 mM Tris/HCl, pH 7.5, 2.5% DMSO and 5mM $CaCl_2$. The rate of substrate hydrolysis was continuously recorded on a Perkin-Elmer LS-5 fluorescence spectrophotometer connected to a R100 chart recorder. The absorbance maximum of substrate occurred at 380 nm and emission maximum was observed at 450 nm. The data, forming a dose-dependent curve, was plotted in FIG. 1. The $IC_{50}$ calculated from FIG. 1 corresponds to that concentration of inhibitory peptide that produced 50% inhibition of calpain activity. The subject peptide inhibited calpain activity with an $IC_{50}$ of 26 μM.

All references with respect to synthetic, preparative and analytic procedures are incorporated herein by reference.

The present invention may be embodied in other specific forms without departing from the spirit or essential attributes thereof and, accordingly, reference should be made to the appended claims, rather than to the foregoing specification, as indicating the scope of the invention.

APPENDIX 1

Kininogen Heavy Chain Domain 2

| | | | | | | | |
|---|---|---|---|---|---|---|---|
| ATOM | 1 | N | CYS | 1 | 148.352 | 83.819 | 84.352 |
| ATOM | 2 | HN | CYS | 1 | 149.065 | 83.809 | 84.469 |
| ATOM | 3 | HN | CYS | 1 | 147.668 | 82.917 | 84.631 |
| ATOM | 4 | HN | CYS | 1 | 147.824 | 83.997 | 83.373 |
| ATOM | 5 | CA | CYS | 1 | 147.470 | 84.875 | 85.190 |
| ATOM | 6 | C | CYS | 1 | 147.825 | 86.268 | 84.842 |
| ATOM | 7 | O | CYS | 1 | 146.840 | 86.969 | 84.504 |
| ATOM | 8 | CB | CYS | 1 | 147.644 | 84.558 | 86.684 |
| ATOM | 9 | SG | CYS | 1 | 146.110 | 84.227 | 87.512 |
| ATOM | 10 | N | LEU | 2 | 149.077 | 86.741 | 84.892 |
| ATOM | 11 | HN | LEU | 2 | 149.734 | 86.089 | 85.056 |
| ATOM | 12 | CA | LEU | 2 | 149.566 | 88.045 | 84.751 |
| ATOM | 13 | C | LEU | 2 | 148.668 | 89.216 | 84.556 |
| ATOM | 14 | O | LEU | 2 | 148.323 | 89.566 | 83.403 |
| ATOM | 15 | CB | LEU | 2 | 150.948 | 88.103 | 84.078 |
| ATOM | 16 | CG | LEU | 2 | 151.989 | 88.607 | 85.388 |
| ATOM | 17 | CD1 | LEU | 2 | 152.870 | 87.455 | 85.583 |
| ATOM | 18 | CD2 | LEU | 2 | 152.865 | 89.687 | 84.451 |
| ATOM | 19 | N | GLY | 3 | 148.176 | 89.956 | 85.546 |
| ATOM | 20 | HN | GLY | 3 | 147.620 | 93.678 | 85.315 |
| ATOM | 21 | CA | GLY | 3 | 148.425 | 89.744 | 86.899 |
| ATOM | 22 | C | GLY | 3 | 147.373 | 93.110 | 87.855 |
| ATOM | 23 | O | GLY | 3 | 147.594 | 91.136 | 88.542 |
| ATOM | 24 | N | CYS | 4 | 146.233 | 89.466 | 88.067 |
| ATOM | 25 | HN | CYS | 4 | 145.730 | 89.717 | 88.819 |
| ATOM | 26 | CA | CYS | 4 | 145.657 | 88.447 | 87.302 |
| ATOM | 27 | C | CYS | 4 | 144.407 | 88.893 | 86.629 |
| ATOM | 28 | O | CYS | 4 | 144.267 | 88.580 | 85.428 |
| ATOM | 29 | CB | CYS | 4 | 145.512 | 87.173 | 88.159 |
| ATOM | 30 | SG | CYS | 4 | 144.869 | 85.790 | 87.252 |
| ATOM | 31 | N | VAL | 5 | 143.398 | 89.595 | 87.138 |
| ATOM | 32 | CA | VAL | 5 | 143.310 | 93.159 | 88.410 |
| ATOM | 33 | C | VAL | 5 | 142.944 | 89.243 | 89.505 |
| ATOM | 34 | O | VAL | 5 | 143.802 | 89.121 | 90.419 |
| ATOM | 35 | CB | VAL | 5 | 142.824 | 91.626 | 88.411 |
| ATOM | 36 | CG1 | VAL | 5 | 141.331 | 91.877 | 88.673 |
| ATOM | 37 | CG2 | VAL | 5 | 143.681 | 92.475 | 89.357 |
| ATOM | 38 | N | HIS | 6 | 141.780 | 88.605 | 89.495 |
| ATOM | 39 | HN | HIS | 6 | 141.248 | 88.691 | 88.725 |
| ATOM | 40 | CA | HIS | 6 | 141.277 | 87.824 | 90.533 |
| ATOM | 41 | C | HIS | 6 | 141.564 | 86.374 | 90.452 |
| ATOM | 42 | O | HIS | 6 | 142.278 | 86.055 | 91.436 |
| ATOM | 43 | CB | HIS | 6 | 139.820 | 88.188 | 90.854 |
| ATOM | 44 | CG | HIS | 6 | 139.748 | 89.140 | 91.966 |
| ATOM | 45 | ND1 | HIS | 6 | 139.722 | 90.444 | 91.890 |
| ATOM | 46 | HND1 | HIS | 6 | 139.754 | 90.942 | 91.094 |
| ATOM | 47 | CD2 | HIS | 6 | 139.693 | 88.811 | 93.310 |
| ATOM | 48 | CE1 | HIS | 6 | 139.643 | 90.946 | 93.098 |
| ATOM | 49 | NB2 | HIS | 6 | 139.620 | 89.950 | 93.959 |
| ATOM | 50 | N | PRO | 7 | 141.170 | 85.479 | 89.513 |
| ATOM | 51 | CA | PRO | 7 | 141.451 | 84.106 | 89.445 |
| ATOM | 52 | C | PRO | 7 | 142.406 | 83.428 | 90.357 |
| ATOM | 53 | O | PRO | 7 | 143.645 | 83.452 | 90.136 |
| ATOM | 54 | CB | PRO | 7 | 141.573 | 83.761 | 87.956 |
| ATOM | 55 | CG | PRO | 7 | 140.747 | 84.851 | 87.278 |
| ATOM | 56 | CD | PRO | 7 | 140.376 | 85.806 | 88.414 |
| ATOM | 57 | N | ILE | 8 | 142.067 | 82.756 | 91.454 |

APPENDIX 1-continued

Kininogen Heavy Chain Domain 2

| ATOM | 58 | HN | ILE | 8 | 142.795 | 82.371 | 91.906 |
|---|---|---|---|---|---|---|---|
| ATOM | 59 | CA | ILE | 8 | 140.820 | 82.514 | 92.071 |
| ATOM | 60 | C | ILE | 8 | 139.579 | 82.532 | 91.276 |
| ATOM | 61 | O | ILE | 8 | 138.880 | 83.575 | 91.257 |
| ATOM | 62 | CB | ILE | 8 | 140.613 | 82.952 | 93.545 |
| ATOM | 63 | CG1 | ILE | 8 | 141.247 | 84.268 | 94.032 |
| ATOM | 64 | CG2 | ILE | 8 | 140.957 | 81.795 | 94.485 |
| ATOM | 65 | CD1 | ILE | 8 | 140.175 | 85.340 | 94.261 |
| ATOM | 66 | N | SER | 9 | 139.281 | 81.419 | 90.612 |
| ATOM | 67 | HN | SER | 9 | 139.846 | 80.683 | 90.762 |
| ATOM | 68 | CA | SER | 9 | 138.231 | 81.215 | 89.710 |
| ATOM | 69 | C | SER | 9 | 137.725 | 79.819 | 89.684 |
| ATOM | 70 | O | SER | 9 | 138.498 | 78.850 | 89.469 |
| ATOM | 71 | CB | SER | 9 | 138.671 | 81.688 | 88.315 |
| ATOM | 72 | OG | SER | 9 | 137.761 | 82.640 | 87.792 |
| ATOM | 73 | HOG | SER | 9 | 137.609 | 83.392 | 88.401 |
| ATOM | 74 | N | THR | 10 | 136.472 | 79.421 | 89.873 |
| ATOM | 75 | HN | THR | 10 | 136.323 | 78.500 | 89.754 |
| ATOM | 76 | CA | THR | 10 | 135.338 | 80.157 | 90.230 |
| ATOM | 77 | C | THR | 10 | 134.536 | 80.843 | 89.190 |
| ATOM | 78 | O | THR | 10 | 133.354 | 80.431 | 89.070 |
| ATOM | 79 | CB | THR | 10 | 135.308 | 80.619 | 91.706 |
| ATOM | 80 | OG1 | THR | 10 | 134.020 | 80.455 | 92.283 |
| ATOM | 81 | HOG1 | THR | 10 | 133.484 | 81.251 | 92.087 |
| ATOM | 82 | CG2 | THR | 10 | 135.838 | 82.029 | 91.989 |
| ATOM | 83 | N | GLN | 11 | 135.020 | 81.822 | 88.423 |
| ATOM | 84 | HN | GLN | 11 | 135.944 | 81.984 | 88.422 |
| ATOM | 85 | CA | GLN | 11 | 134.342 | 82.697 | 87.567 |
| ATOM | 86 | C | GLN | 11 | 133.573 | 83.774 | 88.235 |
| ATOM | 87 | O | GLN | 11 | 132.376 | 83.584 | 88.552 |
| ATOM | 88 | CB | GLN | 11 | 133.780 | 82.094 | 86.264 |
| ATOM | 89 | CG | GLN | 11 | 134.033 | 82.999 | 85.042 |
| ATOM | 90 | CD | GLN | 11 | 135.408 | 82.982 | 84.526 |
| ATOM | 91 | OE1 | GLN | 11 | 136.289 | 83.706 | 85.047 |
| ATOM | 92 | NE2 | GLN | I1 | 135.735 | 82.218 | 83.511 |
| ATOM | 93 | HNE2 | GLN | 11 | 136.618 | 82.217 | 83.192 |
| ATOM | 94 | HNE2 | GLN | 11 | 135.087 | 81.671 | 83.106 |
| ATOM | 95 | N | SER | 12 | 134.078 | 84.967 | 88.528 |
| ATOM | 96 | HN | SER | 12 | 133.556 | 85.557 | 89.040 |
| ATOM | 97 | CA | SER | 12 | 135.333 | 85.440 | 88.146 |
| ATOM | 98 | C | SER | 12 | 136.184 | 85.763 | 89.313 |
| ATOM | 99 | O | SER | 12 | 137.126 | 84.940 | 89.430 |
| ATOM | 100 | CB | SER | 12 | 135.237 | 86.488 | 87.028 |
| ATOM | 101 | OG | SER | 12 | 136.336 | 86.349 | 86.140 |
| ATOM | 102 | HOG | SER | 12 | 136.325 | 85.445 | 85.761 |
| ATOM | 103 | N | PRO | 13 | 136.042 | 86.780 | 90.192 |
| ATOM | 104 | CA | PRO | 13 | 136.409 | 86.699 | 91.547 |
| ATOM | 105 | C | PRO | 13 | 135.691 | 85.729 | 92.410 |
| ATOM | 106 | O | PRO | 13 | 136.371 | 85.208 | 93.333 |
| ATOM | 107 | CB | PRO | 13 | 136.365 | 88.128 | 92.102 |
| ATOM | 108 | CG | PRO | 13 | 136.111 | 89.016 | 90.889 |
| ATOM | 109 | CD | PRO | 13 | 135.526 | 88.035 | 89.876 |
| ATOM | 110 | N | ASP | 14 | 134.403 | 85.425 | 92.225 |
| ATOM | 111 | HN | ASP | 14 | 133.941 | 85.896 | 91.558 |
| ATOM | 112 | CA | ASP | 14 | 133.624 | 84.476 | 92.899 |
| ATOM | 113 | C | ASP | 14 | 132.476 | 84.002 | 92.090 |
| ATOM | 114 | O | ASP | 14 | 132.496 | 82.802 | 91.733 |
| ATOM | 115 | CB | ASP | 14 | 133.243 | 84.950 | 94.313 |
| ATOM | 116 | CG | ASP | 14 | 132.847 | 83.961 | 95.318 |
| ATOM | 117 | OD1 | ASP | 14 | 133.195 | 82.761 | 95.333 |
| ATOM | 118 | OD2 | ASP | 14 | 132.102 | 84.364 | 96.228 |
| ATOM | 119 | N | LEU | 15 | 131.401 | 84.669 | 91.664 |
| ATOM | 120 | HN | LEU | 15 | 130.765 | 84.155 | 91.202 |
| ATOM | 121 | CA | LEU | 15 | 131.087 | 86.026 | 91.806 |
| ATOM | 122 | C | LEU | 15 | 132.080 | 87.008 | 91.291 |
| ATOM | 123 | O | LEU | 15 | 132.652 | 86.804 | 90.192 |
| ATOM | 124 | CB | LEU | 15 | 129.699 | 86.206 | 91.166 |
| ATOM | 125 | CG | LEU | 15 | 128.864 | 87.292 | 91.851 |
| ATOM | 126 | CD1 | LEU | 15 | 128.412 | 88.319 | 90.810 |
| ATOM | 127 | CD2 | LEU | 15 | 127.641 | 86.665 | 92.523 |
| ATOM | 128 | N | GLU | 16 | 132.481 | 88.141 | 91.872 |
| ATOM | 129 | HN | GLU | 16 | 133.174 | 88.581 | 91.413 |
| ATOM | 130 | CA | GLU | 16 | 132.065 | 88.807 | 93.035 |
| ATOM | 131 | C | GLU | 16 | 133.005 | 89.892 | 93.456 |
| ATOM | 132 | O | GLU | 16 | 134.120 | 89.535 | 93.944 |
| ATOM | 133 | CB | GLU | 16 | 131.554 | 87.987 | 94.244 |
| ATOM | 134 | CG | GLU | 16 | 130.229 | 88.426 | 94.900 |
| ATOM | 135 | CD | GLU | 16 | 129.810 | 89.815 | 94.693 |
| ATOM | 136 | OE1 | GLU | 16 | 128.932 | 90.088 | 93.848 |
| ATOM | 137 | OE2 | GLU | 16 | 130.322 | 90.750 | 95.349 |
| ATOM | 138 | N | PRO | 17 | 132.749 | 91.218 | 93.352 |
| ATOM | 139 | CA | PRO | 17 | 133.473 | 92.249 | 93.987 |
| ATOM | 140 | C | PRO | 17 | 133.728 | 92.219 | 95.449 |
| ATOM | 141 | O | PRO | 17 | 134.899 | 92.555 | 95.783 |
| ATOM | 142 | CB | PRO | 17 | 132.865 | 93.586 | 93.541 |
| ATOM | 143 | CG | PRO | 17 | 132.018 | 93.218 | 92.329 |
| ATOM | 144 | CD | PRO | 17 | 131.712 | 91.742 | 92.575 |
| ATOM | 145 | N | ILE | 18 | 132.796 | 91.870 | 96.345 |
| ATOM | 146 | HN | ILE | 18 | 132.002 | 91.504 | 96.000 |
| ATOM | 147 | CA | ILE | 18 | 132.843 | 91.993 | 97.754 |
| ATOM | 148 | C | ILE | 18 | 134.088 | 91.636 | 98.463 |
| ATOM | 149 | O | ILE | 18 | 134.605 | 90.492 | 98.334 |
| ATOM | 150 | CB | ILE | 18 | 131.564 | 91.674 | 98.576 |
| ATOM | 151 | CG1 | ILE | 18 | 130.936 | 90.281 | 98.356 |
| ATOM | 152 | CG2 | ILE | 18 | 130.548 | 92.826 | 98.457 |
| ATOM | 153 | CD1 | ILE | 18 | 130.260 | 89.642 | 99.578 |
| ATOM | 154 | N | LEU | 19 | 134.607 | 92.599 | 99.223 |
| ATOM | 155 | HN | LEU | 19 | 134.090 | 93.383 | 99.276 |
| ATOM | 156 | CA | LEU | 19 | 135.802 | 92.638 | 99.955 |
| ATOM | 157 | C | LEU | 19 | 135.769 | 92.273 | 101.386 |
| ATOM | 158 | O | LEU | 19 | 135.996 | 93.185 | 102.210 |
| ATOM | 159 | CB | LEU | 19 | 137.134 | 92.325 | 99.237 |
| ATOM | 160 | CG | LEU | 19 | 137.621 | 93.422 | 98.272 |
| ATOM | 161 | CD1 | LEU | 19 | 138.172 | 94.664 | 98.988 |
| ATOM | 162 | CD2 | LEU | 19 | 138.748 | 92.854 | 97.409 |
| ATOM | 163 | N | ARG | 20 | 135.540 | 91.110 | 101.974 |
| ATOM | 164 | HN | ARG | 20 | 135.629 | 91.095 | 102.909 |
| ATOM | 165 | CA | ARG | 20 | 135.181 | 89.915 | 101.369 |
| ATOM | 166 | C | ARG | 20 | 134.019 | 89.294 | 102.048 |
| ATOM | 167 | O | ARG | 20 | 132.939 | 89.331 | 101.422 |
| ATOM | 168 | CB | ARG | 20 | 136.413 | 89.009 | 101.198 |
| ATOM | 169 | CG | ARG | 20 | 136.187 | 87.996 | 100.074 |
| ATOM | 170 | CD | ARG | 20 | 137.321 | 88.062 | 99.051 |
| ATOM | 171 | NE | ARG | 20 | 137.046 | 88.933 | 97.995 |
| ATOM | 172 | HNE | ARG | 20 | 136.258 | 89.440 | 98.076 |
| ATOM | 173 | CZ | ARG | 20 | 137.774 | 89.213 | 96.896 |
| ATOM | 174 | NH1 | ARG | 20 | 138.935 | 88.588 | 96.566 |
| ATOM | 175 | HNH1 | ARG | 20 | 139.305 | 88.868 | 95.751 |
| ATOM | 176 | HNH1 | ARG | 20 | 139.367 | 87.962 | 97.118 |
| ATOM | 177 | NH2 | ARG | 20 | 137.328 | 89.947 | 95.979 |
| ATOM | 178 | HNH2 | ARG | 20 | 137.874 | 90.059 | 95.224 |
| ATOM | 179 | HNH2 | ARG | 20 | 136.513 | 90.404 | 96.070 |
| ATOM | 180 | N | HIS | 21 | 133.971 | 88.700 | 103.238 |
| ATOM | 181 | HN | HIS | 21 | 133.147 | 88.348 | 103.520 |
| ATOM | 182 | CA | HIS | 21 | 135.027 | 88.530 | 104.128 |
| ATOM | 183 | C | HIS | 21 | 135.175 | 87.127 | 104.573 |
| ATOM | 184 | O | HIS | 21 | 136.253 | 86.561 | 104.277 |
| ATOM | 185 | CB | HIS | 21 | 135.014 | 89.577 | 105.257 |
| ATOM | 186 | CG | HIS | 21 | 136.366 | 90.019 | 105.617 |
| ATOM | 187 | ND1 | HIS | 21 | 137.078 | 93.937 | 105.017 |
| ATOM | 188 | HND1 | HIS | 21 | 136.835 | 91.441 | 104.272 |
| ATOM | 189 | CD2 | HIS | 21 | 137.129 | 89.533 | 106.668 |
| ATOM | 190 | CE1 | HIS | 21 | 138.238 | 91.045 | 105.620 |
| ATOM | 191 | NE2 | HIS | 21 | 138.268 | 90.188 | 106.619 |
| ATOM | 192 | N | GLY | 22 | 134.339 | 86.344 | 105.242 |
| ATOM | 193 | HN | GLY | 22 | 134.686 | 85.483 | 105.374 |
| ATOM | 194 | CA | GLY | 22 | 133.074 | 86.640 | 105.746 |
| ATOM | 195 | C | GLY | 22 | 131.974 | 86.456 | 104.780 |
| ATOM | 196 | O | GLY | 22 | 131.560 | 87.470 | 104.171 |
| ATOM | 197 | N | ILE | 23 | 131.354 | 85.323 | 104.482 |
| ATOM | 198 | HN | ILE | 23 | 130.708 | 85.349 | 103.799 |
| ATOM | 199 | CA | ILE | 23 | 131.517 | 84.056 | 105.054 |
| ATOM | 200 | C | ILE | 23 | 131.846 | 82.938 | 104.141 |
| ATOM | 201 | O | ILE | 23 | 132.857 | 82.283 | 104.474 |
| ATOM | 202 | CB | ILE | 23 | 130.529 | 83.610 | 106.167 |
| ATOM | 203 | CG1 | ILE | 23 | 129.179 | 84.337 | 106.337 |
| ATOM | 204 | CG2 | ILE | 23 | 131.257 | 83.609 | 107.518 |
| ATOM | 205 | CD1 | ILE | 23 | 128.028 | 83.575 | 105.673 |
| ATOM | 206 | N | GLN | 24 | 131.273 | 82.471 | 103.029 |
| ATOM | 207 | HN | GLN | 24 | 131.598 | 81.629 | 102.774 |
| ATOM | 208 | CA | GLN | 24 | 130.283 | 82.981 | 102.173 |
| ATOM | 209 | C | GLN | 24 | 130.202 | 84.442 | 101.902 |
| ATOM | 210 | O | GLN | 24 | 129.337 | 85.171 | 102.456 |
| ATOM | 211 | CB | GLN | 24 | 128.931 | 82.288 | 102.439 |

APPENDIX 1-continued

Kininogen Heavy Chain Domain 2

| ATOM | 212 | CG | GLN | 24 | 128.644 | 81.061 | 101.555 |
|---|---|---|---|---|---|---|---|
| ATOM | 213 | CD | GLN | 24 | 129.044 | 79.742 | 102.374 |
| ATOM | 214 | OE1 | GLN | 24 | 129.201 | 79.471 | 103.292 |
| ATOM | 215 | NE2 | GLN | 24 | 129.246 | 78.782 | 101.205 |
| ATOM | 216 | HNE2 | GLN | 24 | 129.449 | 77.911 | 101.494 |
| ATOM | 217 | HNE2 | GLN | 24 | 129.188 | 78.977 | 100.287 |
| ATOM | 218 | N | TYR | 25 | 130.968 | 85.166 | 101.103 |
| ATOM | 219 | HN | TYR | 25 | 130.725 | 86.074 | 131.069 |
| ATOM | 220 | CA | TYR | 25 | 132.067 | 84.848 | 100.305 |
| ATOM | 221 | C | TYR | 25 | 133.197 | 84.120 | 100.938 |
| ATOM | 222 | O | TYR | 25 | 133.688 | 84.502 | 102.036 |
| ATOM | 223 | CB | TYR | 25 | 132.499 | 86.262 | 99.881 |
| ATOM | 224 | CG | TYR | 25 | 133.308 | 86.460 | 98.681 |
| ATOM | 225 | CD1 | TYR | 25 | 132.904 | 87.542 | 97.872 |
| ATOM | 226 | CD2 | TYR | 25 | 134.426 | 85.656 | 98.338 |
| ATOM | 227 | CE1 | TYR | 25 | 133.651 | 87.860 | 96.725 |
| ATOM | 228 | CE2 | TYR | 25 | 135.172 | 85.966 | 97.179 |
| ATOM | 229 | CZ | TYR | 25 | 134.770 | 87.069 | 96.396 |
| ATOM | 230 | OH | TYR | 25 | 135.449 | 87.413 | 95.289 |
| ATOM | 231 | HOH | TYR | 25 | 135.079 | 88.161 | 94.777 |
| ATOM | 232 | N | PHE | 26 | 133.785 | 83.042 | 100.434 |
| ATOM | 233 | HN | PHE | 26 | 134.434 | 82.639 | 100.982 |
| ATOM | 234 | CA | PHE | 26 | 133.572 | 82.428 | 99.190 |
| ATOM | 235 | C | PHE | 26 | 132.311 | 81.676 | 98.974 |
| ATOM | 236 | O | PHE | 26 | 131.740 | 81.098 | 99.940 |
| ATOM | 237 | CB | PHE | 26 | 134.797 | 81.519 | 98.983 |
| ATOM | 238 | CG | PHE | 26 | 135.646 | 81.851 | 97.835 |
| ATOM | 239 | CD1 | PHE | 26 | 136.516 | 82.972 | 97.866 |
| ATOM | 240 | CD2 | PHE | 26 | 135.597 | 81.021 | 96.688 |
| ATOM | 241 | CE1 | PHE | 26 | 137.349 | 83.258 | 96.755 |
| ATOM | 242 | CE2 | PHE | 26 | 136.423 | 81.300 | 95.572 |
| ATOM | 243 | CZ | PHE | 26 | 137.294 | 82.417 | 95.616 |
| ATOM | 244 | N | ASN | 27 | 131.809 | 81.634 | 97.738 |
| ATOM | 245 | HN | ASN | 27 | 132.286 | 82.081 | 97.065 |
| ATOM | 246 | CA | ASN | 27 | 130.640 | 81.016 | 97.268 |
| ATOM | 247 | C | ASN | 27 | 130.241 | 79.680 | 97.794 |
| ATOM | 248 | O | ASN | 27 | 129.138 | 79.517 | 98.399 |
| ATOM | 249 | CB | ASN | 27 | 129.555 | 82.110 | 97.138 |
| ATOM | 250 | CG | ASN | 27 | 129.087 | 82.331 | 95.767 |
| ATOM | 251 | OD1 | ASN | 27 | 128.029 | 81.791 | 95.374 |
| ATOM | 252 | ND2 | ASN | 27 | 129.764 | 83.100 | 94.950 |
| ATOM | 253 | HND1 | ASN | 27 | 129.471 | 83.245 | 94.069 |
| ATOM | 254 | HND2 | ASN | 27 | 130.549 | 83.501 | 95.273 |
| ATOM | 255 | N | ASN | 28 | 134.080 | 78.657 | 97.601 |
| ATOM | 256 | HN | ASN | 28 | 131.863 | 78.836 | 97.114 |
| ATOM | 257 | CA | ASN | 28 | 130.907 | 77.345 | 98.057 |
| ATOM | 258 | C | ASN | 28 | 132.084 | 76.737 | 98.723 |
| ATOM | 259 | O | ASN | 28 | 131.972 | 76.597 | 99.960 |
| ATOM | 260 | CB | ASN | 28 | 130.176 | 76.464 | 97.024 |
| ATOM | 261 | CG | ASN | 28 | 129.136 | 75.630 | 97.633 |
| ATOM | 262 | OD1 | ASN | 28 | 129.430 | 74.489 | 98.050 |
| ATOM | 263 | ND2 | ASN | 28 | 127.900 | 76.061 | 97.741 |
| ATOM | 264 | HND2 | ASN | 28 | 127.241 | 75.509 | 98.122 |
| ATOM | 265 | HND2 | ASN | 28 | 127.678 | 76.924 | 97.441 |
| ATOM | 266 | N | ASN | 29 | 133.242 | 76.323 | 98.206 |
| ATOM | 267 | HN | ASN | 29 | 133.864 | 75.949 | 98.803 |
| ATOM | 268 | CA | ASN | 29 | 133.575 | 76.417 | 96.854 |
| ATOM | 269 | C | ASN | 29 | 133.758 | 75.144 | 96.122 |
| ATOM | 270 | O | ASN | 29 | 132.816 | 74.832 | 95.360 |
| ATOM | 271 | CB | ASN | 29 | 134.605 | 77.530 | 96.583 |
| ATOM | 272 | CG | ASN | 29 | 134.572 | 78.097 | 95.229 |
| ATOM | 273 | OD1 | ASN | 29 | 135.458 | 77.768 | 94.410 |
| ATOM | 274 | ND2 | ASN | 29 | 133.643 | 78.947 | 94.857 |
| ATOM | 275 | HD2 | ASN | 29 | 133.707 | 79.366 | 94.019 |
| ATOM | 276 | HND2 | ASN | 29 | 132.923 | 79.140 | 95.429 |
| ATOM | 277 | N | THP | 30 | 134.763 | 74.275 | 96.142 |
| ATOM | 278 | HN | THR | 30 | 134.708 | 73.570 | 95.523 |
| ATOM | 279 | CA | THR | 30 | 135.889 | 74.269 | 96.971 |
| ATOM | 280 | C | THR | 30 | 137.118 | 74.919 | 96.455 |
| ATOM | 281 | O | THR | 30 | 137.566 | 74.647 | 95.303 |
| ATOM | 282 | CB | THR | 30 | 136.035 | 72.867 | 97.610 |
| ATOM | 283 | OG1 | THR | 30 | 136.677 | 72.970 | 98.914 |
| ATOM | 284 | HOG1 | TRR | 30 | 136.126 | 73.688 | 99.403 |
| ATOM | 285 | CG2 | THR | 30 | 136.784 | 71.770 | 96.831 |
| ATOM | 286 | N | GLN | 31 | 137.702 | 75.794 | 97.270 |
| ATOM | 287 | HN | GLN | 31 | 137.343 | 75.863 | 98.136 |
| ATOM | 288 | CA | GLN | 31 | 138.786 | 76.620 | 96.963 |
| ATOM | 289 | C | GLN | 31 | 139.818 | 76.728 | 98.029 |
| ATOM | 290 | O | GLN | 31 | 140.905 | 76.142 | 97.818 |
| ATOM | 291 | CB | GLN | 31 | 138.223 | 77.963 | 96.452 |
| ATOM | 292 | CG | GLN | 31 | 138.989 | 78.654 | 95.308 |
| ATOM | 293 | CD | GLN | 31 | 139.169 | 77.988 | 94.009 |
| ATOM | 294 | OE1 | GLN | 31 | 140.337 | 77.832 | 93.577 |
| ATOM | 295 | NE2 | GLN | 31 | 138.161 | 77.564 | 93.279 |
| ATOM | 296 | HNE2 | GLN | 31 | 138.314 | 77.186 | 92.432 |
| ATOM | 297 | HNE2 | GLN | 31 | 137.286 | 77.639 | 93.613 |
| ATOM | 298 | N | HIS | 32 | 139.169 | 77.371 | 99.194 |
| ATOM | 299 | HN | HIS | 32 | 140.540 | 77.577 | 99.657 |
| ATOM | 300 | CA | HIS | 32 | 138.585 | 77.789 | 99.817 |
| ATOM | 301 | C | HIS | 32 | 138.424 | 79.236 | 100.011 |
| ATOM | 302 | O | HIS | 32 | 137.392 | 79.688 | 99.458 |
| ATOM | 303 | CB | HIS | 32 | 138.288 | 76.977 | 101.091 |
| ATOM | 304 | CG | HIS | 32 | 137.112 | 76.103 | 100.983 |
| ATOM | 305 | ND1 | HIS | 32 | 136.933 | 75.027 | 101.694 |
| ATOM | 306 | HND1 | HIS | 32 | 137.557 | 74.692 | 102.312 |
| ATOM | 307 | CD2 | HIS | 32 | 136.000 | 76.219 | 100.154 |
| ATOM | 308 | CE1 | HIS | 32 | 135.769 | 74.495 | 101.404 |
| ATOM | 309 | NE2 | HIS | 32 | 135.223 | 75.199 | 100.429 |
| ATOM | 310 | N | SER | 33 | 139.280 | 80.003 | 100.706 |
| ATOM | 311 | HN | SER | 33 | 140.128 | 79.622 | 100.837 |
| ATOM | 312 | CA | SER | 33 | 139.035 | 81.286 | 101.245 |
| ATOM | 313 | C | SER | 33 | 138.012 | 81.362 | 102.321 |
| ATOM | 314 | O | SER | 33 | 137.015 | 80.585 | 102.326 |
| ATOM | 315 | CB | SER | 33 | 138.852 | 82.380 | 100.174 |
| ATOM | 316 | OG | SER | 33 | 139.751 | 83.468 | 100.337 |
| ATOM | 317 | HOG | SER | 33 | 139.680 | 83.853 | 101.235 |
| ATOM | 318 | N | SER | 34 | 138.150 | 82.270 | 103.292 |
| ATOM | 319 | HN | SER | 34 | 138.767 | 82.961 | 103.141 |
| ATOM | 320 | CA | SER | 34 | 137.495 | 82.374 | 104.533 |
| ATOM | 321 | C | SER | 34 | 137.616 | 81.279 | 105.523 |
| ATOM | 322 | O | SER | 34 | 137.874 | 81.613 | 106.708 |
| ATOM | 323 | CB | SER | 34 | 136.068 | 82.921 | 104.379 |
| ATOM | 324 | OG | SER | 34 | 135.800 | 83.871 | 105.397 |
| ATOM | 325 | HOG | SER | 34 | 135.972 | 84.769 | 105.043 |
| ATOM | 326 | N | TYR | 35 | 137.451 | 80.018 | 105.138 |
| ATOM | 327 | HN | TYR | 35 | 137.297 | 79.962 | 104.213 |
| ATOM | 328 | CA | TYR | 35 | 137.473 | 78.841 | 105.902 |
| ATOM | 329 | C | TYR | 35 | 138.829 | 78.296 | 106.128 |
| ATOM | 330 | O | TYR | 35 | 139.580 | 77.993 | 105.155 |
| ATOM | 331 | CB | TYR | 35 | 136.501 | 77.724 | 105.433 |
| ATOM | 332 | CG | TYR | 35 | 135.286 | 78.119 | 104.707 |
| ATOM | 333 | CD1 | TYR | 35 | 134.083 | 78.401 | 105.405 |
| ATOM | 334 | CD2 | TYR | 35 | 135.357 | 78.215 | 103.296 |
| ATOM | 335 | CE1 | TYR | 35 | 132.959 | 78.867 | 104.683 |
| ATOM | 336 | CE2 | TYR | 35 | 134.250 | 78.712 | 102.576 |
| ATOM | 337 | CZ | TYR | 35 | 133.073 | 79.049 | 103.283 |
| ATOM | 338 | OH | TYR | 35 | 132.045 | 79.552 | 102.571 |
| ATOM | 339 | HOH | TYR | 35 | 131.144 | 79.645 | 102.943 |
| ATOM | 340 | N | PHE | 36 | 139.206 | 78.142 | 107.393 |
| ATOM | 341 | HN | PHE | 36 | 138.622 | 78.474 | 108.052 |
| ATOM | 342 | CA | PHE | 36 | 140.379 | 77.528 | 107.844 |
| ATOM | 343 | C | PHE | 36 | 140.230 | 76.070 | 108.056 |
| ATOM | 344 | O | PHE | 36 | 139.340 | 75.613 | 108.830 |
| ATOM | 345 | CB | PHE | 36 | 140.974 | 78.329 | 109.022 |
| ATOM | 346 | CG | PHE | 36 | 142.151 | 77.734 | 109.668 |
| ATOM | 347 | CD1 | PHE | 36 | 143.389 | 77.621 | 108.980 |
| ATOM | 348 | CD2 | PHE | 36 | 142.028 | 77.267 | 111.002 |
| ATOM | 349 | CE1 | PHE | 36 | 144.499 | 77.014 | 109.617 |
| ATOM | 350 | CE2 | PHE | 36 | 143.138 | 76.666 | 111.646 |
| ATOM | 351 | CZ | PHE | 36 | 144.363 | 76.542 | 110.945 |
| ATOM | 352 | N | MET | 37 | 141.086 | 75.295 | 107.389 |
| ATOM | 353 | HN | MET | 37 | 141.749 | 75.742 | 106.894 |
| ATOM | 354 | CA | MET | 37 | 141.141 | 73.892 | 107.324 |
| ATOM | 355 | C | MET | 37 | 140.142 | 73.243 | 106.450 |
| ATOM | 356 | O | MET | 37 | 138.905 | 73.386 | 106.652 |
| ATOM | 357 | CB | MET | 37 | 141.436 | 73.144 | 108.645 |
| ATOM | 358 | CG | MET | 37 | 142.856 | 73.370 | 109.192 |
| ATOM | 359 | SD | MET | 37 | 144.093 | 72.637 | 108.154 |
| ATOM | 360 | CE | MET | 37 | 145.619 | 73.083 | 108.932 |
| ATOM | 361 | N | LEU | 38 | 140.642 | 72.515 | 105.453 |
| ATOM | 362 | HN | LEU | 38 | 141.562 | 72.329 | 105.516 |
| ATOM | 363 | CA | LEU | 38 | 140.004 | 71.995 | 104.315 |
| ATOM | 364 | C | LEU | 38 | 139.865 | 72.996 | 103.240 |
| ATOM | 365 | O | LEU | 38 | 139.057 | 73.960 | 103.358 |

APPENDIX 1-continued

Kininogen Heavy Chain Domain 2

| | | | | | | | |
|---|---|---|---|---|---|---|---|
| ATOM | 366 | CB | LEU | 38 | 138.798 | 71.052 | 104.532 |
| ATOM | 367 | CG | LEU | 38 | 138.546 | 70.138 | 103.324 |
| ATOM | 368 | CD1 | LEU | 38 | 138.327 | 68.701 | 103.803 |
| ATOM | 369 | CD2 | LEU | 38 | 137.309 | 70.600 | 102.544 |
| ATOM | 370 | N | ASN | 39 | 140.650 | 72.793 | 102.183 |
| ATOM | 371 | HN | ASN | 39 | 141.075 | 71.955 | 102.139 |
| ATOM | 372 | CA | ASN | 39 | 140.928 | 73.684 | 101.135 |
| ATOM | 373 | C | ASN | 39 | 141.672 | 74.931 | 101.479 |
| ATOM | 374 | O | ASN | 39 | 141.846 | 75.256 | 102.694 |
| ATOM | 375 | CB | ASN | 39 | 139.759 | 73.766 | 100.130 |
| ATOM | 376 | CG | ASN | 39 | 139.887 | 72.825 | 99.012 |
| ATOM | 377 | OD1 | ASN | 39 | 139.611 | 71.609 | 99.152 |
| ATOM | 378 | ND2 | ASN | 39 | 140.293 | 73.276 | 97.853 |
| ATOM | 379 | HND2 | ASN | 39 | 140.380 | 72.699 | 97.115 |
| ATOM | 380 | HND2 | ASN | 39 | 140.495 | 74.190 | 97.778 |
| ATOM | 381 | N | GLU | 40 | 142.170 | 75.707 | 100.510 |
| ATOM | 382 | HN | GLU | 40 | 141.820 | 75.628 | 99.642 |
| ATOM | 383 | CA | GLU | 40 | 143.189 | 76.661 | 100.667 |
| ATOM | 384 | C | GLU | 40 | 142.876 | 78.012 | 100.139 |
| ATOM | 385 | O | GLU | 40 | 141.946 | 78.639 | 100.732 |
| ATOM | 386 | CB | GLU | 40 | 144.626 | 76.089 | 100.521 |
| ATOM | 387 | CG | GLU | 40 | 144.999 | 75.298 | 99.246 |
| ATOM | 388 | CD | GLU | 40 | 145.029 | 76.034 | 97.977 |
| ATOM | 389 | OE1 | GLU | 40 | 145.691 | 77.083 | 97.810 |
| ATOM | 390 | OE2 | GLU | 40 | 144.379 | 75.621 | 96.995 |
| ATOM | 391 | N | VAL | 41 | 143.532 | 78.535 | 99.103 |
| ATOM | 392 | HN | VAL | 41 | 144.202 | 78.005 | 98.713 |
| ATOM | 393 | CA | VAL | 41 | 143.363 | 79.793 | 98.503 |
| ATOM | 394 | C | VAL | 41 | 144.596 | 80.539 | 98.178 |
| ATOM | 395 | O | VAL | 41 | 144.516 | 81.775 | 98.377 |
| ATOM | 396 | CB | VAL | 41 | 142.375 | 79.923 | 97.317 |
| ATOM | 397 | CG1 | VAL | 41 | 142.368 | 78.841 | 96.231 |
| ATOM | 398 | CG2 | VAL | 41 | 140.957 | 80.270 | 97.770 |
| ATOM | 399 | N | LYS | 42 | 145.710 | 79.974 | 97.706 |
| ATOM | 400 | HN | LYS | 42 | 145.715 | 79.035 | 97.677 |
| ATOM | 401 | CA | LYS | 42 | 146.854 | 80.649 | 97.263 |
| ATOM | 402 | C | LYS | 42 | 146.849 | 80.925 | 95.802 |
| ATOM | 403 | O | LYS | 42 | 147.573 | 80.280 | 94.982 |
| ATOM | 404 | CB | LYS | 42 | 148.078 | 79.949 | 97.878 |
| ATOM | 405 | CG | LYS | 42 | 149.294 | 80.876 | 97.933 |
| ATOM | 406 | CD | LYS | 42 | 150.150 | 80.498 | 99.147 |
| ATOM | 407 | CE | LYS | 42 | 151.389 | 81.388 | 99.301 |
| ATOM | 408 | NZ | LYS | 42 | 151.084 | 82.506 | 100.186 |
| ATOM | 409 | HNZ | LYS | 42 | 151.908 | 83.088 | 100.328 |
| ATOM | 410 | HNZ | LYS | 42 | 150.318 | 83.053 | 99.795 |
| ATOM | 411 | HNZ | LYS | 42 | 150.776 | 82.167 | 101.096 |
| ATOM | 412 | N | ARG | 43 | 146.029 | 81.891 | 95.391 |
| ATOM | 413 | HN | ARG | 43 | 145.563 | 82.360 | 96.057 |
| ATOM | 414 | CA | ARG | 43 | 145.783 | 82.270 | 94.067 |
| ATOM | 415 | C | ARG | 43 | 145.941 | 83.710 | 93.774 |
| ATOM | 416 | O | ARG | 43 | 146.565 | 83.966 | 92.700 |
| ATOM | 417 | CB | ARG | 43 | 144.493 | 81.593 | 93.565 |
| ATOM | 418 | CG | ARG | 43 | 144.667 | 80.731 | 92.296 |
| ATOM | 419 | CD | ARG | 43 | 145515 | 79.450 | 92.419 |
| ATOM | 420 | NE | ARG | 43 | 144.819 | 78.321 | 92.876 |
| ATOM | 421 | HNE | ARG | 43 | 144.190 | 77.961 | 92.276 |
| ATOM | 422 | CZ | ARG | 43 | 144.930 | 77.691 | 94.050 |
| ATOM | 423 | NH1 | ARG | 43 | 144.192 | 76.632 | 94.273 |
| ATOM | 424 | HNH1 | ARG | 43 | 144.241 | 76.238 | 95.125 |
| ATOM | 425 | HNH1 | ARG | 43 | 143.632 | 76.280 | 93.606 |
| ATOM | 426 | NH2 | ARG | 43 | 145.712 | 78.012 | 95.061 |
| ATOM | 427 | HNH2 | ARG | 43 | 145.667 | 77.548 | 95.875 |
| ATOM | 428 | HNH2 | ARG | 43 | 146.325 | 78.721 | 94.982 |
| ATOM | 429 | N | ALA | 44 | 145.479 | 84.678 | 94.591 |
| ATOM | 430 | HN | ALA | 44 | 144.962 | 84.425 | 95.333 |
| ATOM | 431 | CA | ALA | 44 | 145.688 | 86.067 | 94.498 |
| ATOM | 432 | C | ALA | 44 | 147.067 | 86.550 | 94.793 |
| ATOM | 433 | O | ALA | 44 | 147.221 | 87.612 | 95.453 |
| ATOM | 434 | CB | ALA | 44 | 144.968 | 86.688 | 93.286 |
| ATOM | 435 | N | GLN | 45 | 148.104 | 85.836 | 94.343 |
| ATOM | 436 | HN | GLN | 45 | 147.809 | 85.154 | 93.773 |
| ATOM | 437 | CA | GLN | 45 | 149.480 | 85.932 | 94.590 |
| ATOM | 438 | C | GLN | 45 | 150.316 | 85.364 | 93.497 |
| ATOM | 439 | O | GLN | 45 | 153.011 | 84.303 | 92.896 |
| ATOM | 440 | CB | GLN | 45 | 149.762 | 85.172 | 95.898 |
| ATOM | 441 | CG | GLN | 45 | 150.625 | 86.019 | 96.841 |
| ATOM | 442 | CD | GLN | 45 | 151.572 | 85.288 | 97.693 |
| ATOM | 443 | OE1 | GLN | 45 | 152.328 | 84.374 | 97.270 |
| ATOM | 444 | NE2 | GLN | 45 | 151.624 | 85.626 | 98.949 |
| ATOM | 445 | HNE2 | GLN | 45 | 152.224 | 85.197 | 99.531 |
| ATOM | 446 | HNE2 | GLN | 45 | 151.050 | 86.304 | 99.254 |
| ATOM | 447 | N | ARG | 46 | 151.447 | 85.846 | 93.006 |
| ATOM | 448 | HN | ARG | 46 | 151.822 | 85.346 | 92.303 |
| ATOM | 449 | CA | ARG | 46 | 152.162 | 86.988 | 93.377 |
| ATOM | 450 | C | ARG | 46 | 152.387 | 87.943 | 92.263 |
| ATOM | 451 | O | ARG | 46 | 152.662 | 87.539 | 91.100 |
| ATOM | 452 | CB | ARG | 46 | 153.510 | 86.577 | 93.996 |
| ATOM | 453 | CG | ARG | 46 | 153.509 | 86.947 | 95.480 |
| ATOM | 454 | CD | ARG | 46 | 154.910 | 87.056 | 96.087 |
| ATOM | 455 | NE | ARG | 46 | 154.850 | 87.323 | 97.461 |
| ATOM | 456 | HNE | ARG | 46 | 155.049 | 86.602 | 98.030 |
| ATOM | 457 | CZ | ARG | 46 | 154.554 | 88.453 | 98.107 |
| ATOM | 458 | NH1 | ARG | 46 | 154.699 | 88.390 | 99.405 |
| ATOM | 459 | HNH1 | ARG | 46 | 154.707 | 89.158 | 99.945 |
| ATOM | 460 | HNH1 | ARG | 46 | 154.795 | 87.541 | 99.797 |
| ATOM | 461 | NH2 | ARG | 46 | 154.136 | 89.600 | 97.608 |
| ATOM | 462 | HNH2 | ARG | 46 | 153.825 | 90.258 | 98.200 |
| ATOM | 463 | HNH2 | ARG | 46 | 154.137 | 89.749 | 96.679 |
| ATOM | 464 | N | GLN | 47 | 152.324 | 89.267 | 92.366 |
| ATOM | 465 | HN | GLN | 47 | 152.510 | 89.734 | 91.573 |
| ATOM | 466 | CA | GLN | 47 | 152.028 | 90.085 | 93.463 |
| ATOM | 467 | C | GLN | 47 | 153.123 | 90.713 | 94.230 |
| ATOM | 468 | O | GLN | 47 | 154.046 | 90.022 | 94.728 |
| ATOM | 469 | CB | GLN | 47 | 150.651 | 89.911 | 94.138 |
| ATOM | 470 | CG | GLN | 47 | 149.786 | 91.189 | 94.070 |
| ATOM | 471 | CD | GLN | 47 | 149.820 | 91.966 | 92.820 |
| ATOM | 472 | OE1 | GLN | 47 | 149.488 | 91.455 | 91.727 |
| ATOM | 473 | NE2 | GLN | 47 | 150.204 | 93.219 | 92.829 |
| ATOM | 474 | HNE1 | GLN | 47 | 150.365 | 93.652 | 92.011 |
| ATOM | 475 | HNE2 | GLN | 47 | 150.315 | 93.670 | 93.645 |
| ATOM | 476 | N | VAL | 48 | 153.051 | 92.037 | 94.339 |
| ATOM | 477 | HN | VAL | 48 | 152.248 | 92.413 | 94.027 |
| ATOM | 478 | CA | VAL | 48 | 153.971 | 92.965 | 94.834 |
| ATOM | 479 | C | VAL | 48 | 155.354 | 92.913 | 94.294 |
| ATOM | 480 | O | VAL | 48 | 156.266 | 92.335 | 94.928 |
| ATOM | 481 | CB | VAL | 48 | 153.623 | 93.614 | 96.196 |
| ATOM | 482 | CG1 | VAL | 48 | 154.471 | 93.214 | 97.409 |
| ATOM | 483 | CG2 | VAL | 48 | 153.630 | 95.144 | 96.091 |
| ATOM | 484 | N | VAL | 49 | 155.727 | 93.448 | 93.141 |
| ATOM | 485 | HN | VAL | 49 | 156.647 | 93.472 | 92.955 |
| ATOM | 486 | CA | VAL | 49 | 154.859 | 93.972 | 92.169 |
| ATOM | 487 | C | VAL | 49 | 154.543 | 92.972 | 91.137 |
| ATOM | 488 | O | VAL | 49 | 153.360 | 92.536 | 91.161 |
| ATOM | 489 | CB | VAL | 49 | 154.976 | 95.419 | 91.630 |
| ATOM | 490 | CG1 | VAL | 49 | 153.749 | 96.222 | 92.074 |
| ATOM | 491 | CG2 | VAL | 49 | 156.243 | 96.243 | 91.918 |
| ATOM | 492 | N | ALA | 50 | 155.463 | 92.564 | 90.258 |
| ATOM | 493 | HN | ALA | 50 | 156.289 | 93.012 | 90.277 |
| ATOM | 494 | CA | ALA | 50 | 155.333 | 91.538 | 89.318 |
| ATOM | 495 | C | ALA | 50 | 154.799 | 90.256 | 89.859 |
| ATOM | 496 | O | ALA | 5G | 155.419 | 89.611 | 90.748 |
| ATOM | 497 | CB | ALA | 50 | 156.618 | 91.406 | 88.487 |
| ATOM | 498 | N | GLY | 51 | 153.653 | 89.700 | 89.479 |
| ATOM | 499 | HN | GLY | 51 | 153.370 | 88.950 | 89.968 |
| ATOM | 500 | CA | GLY | 51 | 152.818 | 90.108 | 88.442 |
| ATOM | 501 | C | GLY | 51 | 151.376 | 90.188 | 88.756 |
| ATOM | 502 | O | GLY | 51 | 150.762 | 89.134 | 89.039 |
| ATOM | 503 | N | LEU | 52 | 150.627 | 91.284 | 88.751 |
| ATOM | 504 | HN | LEU | 52 | 149.698 | 91.169 | 88.830 |
| ATOM | 505 | CA | LEU | 52 | 151.046 | 92.609 | 88.628 |
| ATOM | 506 | C | LEU | 52 | 150.248 | 93.585 | 89.404 |
| ATOM | 507 | O | LEU | 52 | 150.896 | 94.359 | 90.151 |
| ATOM | 508 | CB | LEU | 52 | 151.123 | 92.971 | 87.128 |
| ATOM | 509 | CG | LEU | 52 | 152.036 | 94.166 | 86.828 |
| ATOM | 510 | CD1 | LEU | 52 | 153.433 | 93.688 | 86.419 |
| ATOM | 511 | CD2 | LEU | 52 | 151.423 | 94.967 | 85.678 |
| ATOM | 512 | N | ASN | 53 | 148.917 | 93.641 | 89.309 |
| ATOM | 513 | HN | ASN | 53 | 148.488 | 92.853 | 89.028 |
| ATOM | 514 | CA | ASN | 53 | 148.093 | 94.745 | 89.564 |
| ATOM | 515 | C | ASN | 53 | 147.801 | 94.952 | 91.001 |
| ATOM | 516 | O | ASN | 53 | 148.401 | 95.900 | 91.567 |
| ATOM | 517 | CB | ASN | 53 | 146.845 | 94.727 | 88.642 |
| ATOM | 518 | CG | ASN | 53 | 147.036 | 94.581 | 87.190 |
| ATOM | 519 | OD1 | ASN | 53 | 147.042 | 95.597 | 86.463 |

APPENDIX 1-continued

Kininogen Heavy Chain Domain 2

| ATOM | 520 | ND2 | ASN | 53 | 147.198 | 93.396 | 86.645 |
|------|-----|------|-----|----|---------|--------|--------|
| ATOM | 521 | HND2 | ASN | 53 | 147.254 | 93.301 | 85.711 |
| ATOM | 522 | HND2 | ASN | 53 | 147.261 | 92.645 | 87.206 |
| ATOM | 523 | N | PHE | 54 | 146.942 | 94.155 | 91.638 |
| ATOM | 524 | HN | PHE | 54 | 146.501 | 93.529 | 91.093 |
| ATOM | 525 | CA | PHE | 54 | 146.599 | 94.102 | 92.995 |
| ATOM | 526 | C | PHE | 54 | 146.374 | 92.721 | 93.494 |
| ATOM | 527 | O | PHE | 54 | 146.797 | 92.461 | 94.650 |
| ATOM | 528 | CB | PHE | 54 | 145.512 | 95.128 | 93.394 |
| ATOM | 529 | CG | PHE | 54 | 144.115 | 94.801 | 93.085 |
| ATOM | 530 | CD1 | PHE | 54 | 143.351 | 94.023 | 93.997 |
| ATOM | 531 | CD2 | PHE | 54 | 143.536 | 95.270 | 91.877 |
| ATOM | 532 | CE1 | PHE | 54 | 142.006 | 93.701 | 93.695 |
| ATOM | 533 | CE2 | PHE | 54 | 142.188 | 94.955 | 91.576 |
| ATOM | 534 | CZ | PHE | 54 | 141.435 | 94.169 | 92.485 |
| ATOM | 535 | N | ARG | 55 | 145.754 | 91.798 | 92.744 |
| ATOM | 536 | HN | ARG | 55 | 145.415 | 92.113 | 91.926 |
| ATOM | 537 | CA | ARG | 55 | 145.537 | 90.436 | 92.986 |
| ATOM | 538 | C | ARG | 55 | 144.580 | 90.132 | 94.084 |
| ATOM | 539 | O | ARG | 55 | 143.398 | 90.537 | 93.901 |
| ATOM | 540 | CB | ARG | 55 | 146.852 | 89.630 | 92.884 |
| ATOM | 541 | CG | ARG | 55 | 147.177 | 89.046 | 91.506 |
| ATOM | 542 | CD | ARG | 55 | 148.219 | 87.952 | 91.754 |
| ATOM | 543 | NE | ARG | 55 | 148.909 | 87.555 | 90.613 |
| ATOM | 544 | HNE | ARG | 55 | 149.460 | 88.186 | 90.187 |
| ATOM | 545 | CZ | ARG | 55 | 148.931 | 86.379 | 89.997 |
| ATOM | 546 | NH1 | ARG | 55 | 149.741 | 86.395 | 88.969 |
| ATOM | 547 | HNH1 | ARG | 55 | 149.875 | 85.643 | 88.421 |
| ATOM | 548 | HNH1 | ARG | 55 | 150.178 | 87.212 | 88.819 |
| ATOM | 549 | NH2 | ARG | 55 | 148.287 | 85.251 | 90.261 |
| ATOM | 550 | HNH2 | ARG | 55 | 148.379 | 84.530 | 89.665 |
| ATOM | 551 | HNH2 | ARG | 55 | 147.742 | 85.146 | 91.019 |
| ATOM | 552 | N | ILE | 56 | 144.925 | 89.465 | 95.192 |
| ATOM | 553 | HN | ILE | 56 | 145.765 | 89.043 | 95.207 |
| ATOM | 554 | CA | ILE | 56 | 144.194 | 89.281 | 96.368 |
| ATOM | 555 | C | ILE | 56 | 143.197 | 88.191 | 96.365 |
| ATOM | 556 | O | ILE | 56 | 142.189 | 88.235 | 95.611 |
| ATOM | 557 | CB | ILE | 56 | 143.948 | 90.562 | 97.211 |
| ATOM | 558 | CG1 | ILE | 56 | 144.230 | 90.343 | 98.706 |
| ATOM | 559 | CG2 | ILE | 56 | 142.570 | 91.23G | 97.057 |
| ATOM | 560 | CD1 | ILE | 56 | 145.714 | 90.518 | 99.053 |
| ATOM | 561 | N | THR | 57 | 143.433 | 87.190 | 97.203 |
| ATOM | 562 | HN | THR | 57 | 144.297 | 87.119 | 97.566 |
| ATOM | 563 | CA | THR | 57 | 142.482 | 86.239 | 97.602 |
| ATOM | 564 | C | THR | 57 | 141.553 | 86.816 | 98.607 |
| ATOM | 565 | O | THR | 57 | 140.334 | 86.663 | 98.331 |
| ATOM | 566 | CB | THR | 57 | 142.965 | 84.799 | 97.906 |
| ATOM | 567 | OG1 | THR | 57 | 144.086 | 84.302 | 97.180 |
| ATOM | 568 | HOG1 | THR | 57 | 144.282 | 83.418 | 97.554 |
| ATOM | 569 | CG2 | THR | 57 | 141.857 | 83.778 | 97.629 |
| ATOM | 570 | N | TYR | 58 | 141.970 | 87.461 | 99.711 |
| ATOM | 571 | HN | TYR | 58 | 142.887 | 87.380 | 99.897 |
| ATOM | 572 | CA | TYR | 58 | 141.249 | 88.251 | 100.623 |
| ATOM | 573 | C | TYR | 58 | 140.469 | 87.500 | 101.632 |
| ATOM | 574 | O | TYR | 58 | 139.305 | 87.095 | 101.368 |
| ATOM | 575 | CB | TYR | 58 | 140.535 | 89.442 | 99.933 |
| ATOM | 576 | CC | TYR | 58 | 140.310 | 93.675 | 100.694 |
| ATOM | 577 | CD1 | TYR | 58 | 139.472 | 90.690 | 101.839 |
| ATOM | 578 | CD2 | TYR | 58 | 140.949 | 91.856 | 100.239 |
| ATOM | 579 | CE1 | TYR | 58 | 139.256 | 91.909 | 102.520 |
| ATOM | 580 | CE2 | TYR | 58 | 140.730 | 93.076 | 100.920 |
| ATOM | 581 | CZ | TYR | 58 | 139.884 | 93.087 | 102.054 |
| ATOM | 582 | OH | TYR | 58 | 139.669 | 94.246 | 102.713 |
| ATOM | 583 | HOH | TYR | 58 | 139.087 | 94.255 | 103.502 |
| ATOM | 584 | N | SER | 59 | 141.064 | 87.289 | 102.806 |
| ATOM | 585 | HN | SER | 59 | 141.931 | 87.641 | 102.891 |
| ATOM | 586 | CA | SER | 59 | 140.573 | 86.612 | 103.934 |
| ATOM | 587 | C | SER | 59 | 140.383 | 85.146 | 103.820 |
| ATOM | 588 | O | SER | 59 | 139.641 | 84.650 | 102.946 |
| ATOM | 589 | CB | SER | 59 | 139.450 | 87.337 | 104.691 |
| ATOM | 590 | OG | SER | 59 | 139.991 | 87.983 | 105.833 |
| ATOM | 591 | HOG | SER | 59 | 139.394 | 88.709 | 106.111 |
| ATOM | 592 | N | ILE | 60 | 140.959 | 84.231 | 104.585 |
| ATOM | 593 | HN | ILE | 60 | 140.688 | 83.342 | 104.446 |
| ATOM | 594 | CA | ILE | 60 | 141.930 | 84.432 | 105.577 |
| ATOM | 595 | C | ILE | 60 | 143.186 | 85.009 | 105.033 |
| ATOM | 596 | O | ILE | 60 | 143.506 | 86.114 | 105.526 |
| ATOM | 597 | CB | ILE | 60 | 142.188 | 83.299 | 106.612 |
| ATOM | 598 | CG1 | ILE | 60 | 141.262 | 82.065 | 106.678 |
| ATOM | 599 | CG2 | ILE | 60 | 142.180 | 83.923 | 108.012 |
| ATOM | 600 | CD1 | ILE | 60 | 141.691 | 80.932 | 105.738 |
| ATOM | 601 | N | VAL | 61 | 143.990 | 84.508 | 104.092 |
| ATOM | 602 | HN | VAL | 61 | 144.694 | 85.046 | 103.778 |
| ATOM | 603 | CA | VAL | 61 | 143.866 | 83.233 | 103.510 |
| ATOM | 604 | C | VAL | 61 | 144.933 | 82.321 | 103.997 |
| ATOM | 605 | C | VAL | 64 | 144.858 | 81.945 | 105.194 |
| ATOM | 606 | CB | VAL | 61 | 143.524 | 83.146 | 101.995 |
| ATOM | 607 | CG1 | VAL | 61 | 142.593 | 81.959 | 101.730 |
| ATOM | 608 | CC2 | VAL | 61 | 142.931 | 84.361 | 101.264 |
| ATOM | 609 | N | GLN | 62 | 145.991 | 81.806 | 103.388 |
| ATOM | 610 | HN | GLN | 62 | 146.626 | 81.425 | 103.968 |
| ATOM | 611 | CA | GLN | 62 | 146.321 | 81.715 | 102.032 |
| ATOM | 612 | C | GLN | 62 | 146.880 | 80.380 | 101.722 |
| ATOM | 613 | O | GLN | 62 | 146.326 | 79.756 | 100.784 |
| ATOM | 614 | CB | GLN | 62 | 147.141 | 82.893 | 101.478 |
| ATOM | 615 | CG | GLN | 62 | 146.653 | 83.199 | 100.050 |
| ATOM | 616 | CD | GLN | 62 | 147.488 | 84.000 | 99.146 |
| ATOM | 617 | OE1 | GLN | 62 | 148.739 | 83.998 | 99.205 |
| ATOM | 618 | NE2 | GLN | 62 | 146.910 | 84.742 | 98.230 |
| ATOM | 619 | HNE2 | GLN | 62 | 147.419 | 85.358 | 97.736 |
| ATOM | 620 | HNE2 | GLN | 62 | 145.991 | 84.661 | 98.053 |
| ATOM | 621 | N | THR | 63 | 147.908 | 79.862 | 102.406 |
| ATOM | 622 | HN | THR | 63 | 148.591 | 80.465 | 102.642 |
| ATOM | 623 | CA | THR | 63 | 148.058 | 78.522 | 102.813 |
| ATOM | 624 | C | THR | 63 | 146.903 | 78.038 | 103.616 |
| ATOM | 625 | O | THR | 63 | 145.751 | 77.930 | 103.110 |
| ATOM | 626 | CB | THR | 63 | 148.728 | 77.616 | 101.748 |
| ATOM | 627 | OG1 | THR | 63 | 150.084 | 78.024 | 101.556 |
| ATOM | 628 | HOG1 | THR | 63 | 150.436 | 78.356 | 102.407 |
| ATOM | 629 | CG2 | THR | 63 | 148.785 | 76.117 | 102.079 |
| ATOM | 630 | N | ASN | 64 | 147.124 | 77.730 | 104.886 |
| ATOM | 631 | HN | ASN | 64 | 148.006 | 77.524 | 105.135 |
| ATOM | 632 | CA | ASN | 64 | 146.171 | 77.688 | 105.911 |
| ATOM | 633 | C | ASN | 64 | 146.610 | 78.441 | 107.111 |
| ATOM | 634 | O | ASN | 64 | 145.853 | 79.364 | 107.496 |
| ATOM | 635 | CB | ASN | 64 | 145.574 | 76.288 | 106.179 |
| ATOM | 636 | CG | ASN | 64 | 144.288 | 76.067 | 105.498 |
| ATOM | 637 | OD1 | ASN | 64 | 143.234 | 76.594 | 105.928 |
| ATOM | 638 | ND2 | ASN | 64 | 144.231 | 75.312 | 104.425 |
| ATOM | 639 | HND2 | ASN | 64 | 143.435 | 75.247 | 103.928 |
| ATOM | 640 | HND2 | ASN | 64 | 144.993 | 74.836 | 104.149 |
| ATOM | 641 | N | CYS | 65 | 147.704 | 78.291 | 107.852 |
| ATOM | 642 | HN | CYS | 65 | 147.807 | 78.953 | 108.509 |
| ATOM | 643 | CA | CYS | 65 | 148.662 | 77.276 | 107.727 |
| ATOM | 644 | C | CYS | 65 | 149.755 | 77.580 | 106.785 |
| ATOM | 645 | D | CYS | 65 | 149.757 | 76.878 | 105.740 |
| ATOM | 646 | CB | CYS | 65 | 149.191 | 76.684 | 109.046 |
| ATOM | 647 | SG | CYS | 65 | 147.981 | 75.852 | 110.043 |
| ATOM | 648 | N | SEH | 66 | 150.671 | 78.523 | 107.023 |
| ATOM | 649 | CA | SER | 66 | 151.821 | 78.916 | 106.322 |
| ATOM | 650 | C | SER | 66 | 151.618 | 79.632 | 105.048 |
| ATOM | 651 | O | SEB | 66 | 151.071 | 79.038 | 104.073 |
| ATOM | 652 | CB | SER | 66 | 152.894 | 77.809 | 106.255 |
| ATOM | 653 | OG | SER | 66 | 154.197 | 78.343 | 106.052 |
| ATOM | 654 | HOG | SER | 66 | 154.439 | 78.916 | 106.808 |
| ATOM | 655 | N | LYS | 67 | 152.041 | 80.894 | 105.003 |
| ATOM | 656 | HN | LYS | 67 | 152.283 | 81.307 | 105.813 |
| ATOM | 657 | CA | LYS | 67 | 152.161 | 81.641 | 103.831 |
| ATOM | 658 | C | LYS | 67 | 150.997 | 82.423 | 103.368 |
| ATOM | 659 | O | LYS | 67 | 150.085 | 81.740 | 102.848 |
| ATOM | 660 | CB | LYS | 67 | 153.576 | 82.179 | 103.596 |
| ATOM | 661 | CG | LYS | 67 | 154.216 | 81.366 | 102.467 |
| ATOM | 662 | CD | LYS | 67 | 155.545 | 82.014 | 102.087 |
| ATOM | 663 | CE | LYS | 67 | 155.734 | 82.000 | 100.571 |
| ATOM | 664 | NZ | LYS | 67 | 156.348 | 83.253 | 100.145 |
| ATOM | 665 | HNZ1 | LYS | 67 | 155.739 | 84.042 | 100.354 |
| ATOM | 666 | HNZ2 | LYS | 67 | 156.498 | 83.219 | 99.137 |
| ATOM | 667 | HNZ3 | LYS | 67 | 157.253 | 83.335 | 100.607 |
| ATOM | 668 | N | GLU | 68 | 150.729 | 83.723 | 103.389 |
| ATOM | 669 | HN | GLU | 68 | 149.913 | 83.970 | 102.992 |
| ATOM | 670 | CA | GLU | 68 | 151.484 | 84.770 | 103.918 |
| ATOM | 671 | C | GLU | 68 | 150.720 | 85.384 | 105.031 |
| ATOM | 672 | O | GLU | 68 | 151.049 | 85.037 | 106.183 |
| ATOM | 673 | CB | GLU | 68 | 151.934 | 85.753 | 102.816 |

APPENDIX 1-continued

Kininogen Heavy Chain Domain 2

| ATOM | 674 | CG | GLU | 68 | 153.444 | 85.722 | 102.523 |
|------|-----|-----|-----|----|---------|--------|---------|
| ATOM | 675 | CD | GLU | 68 | 153.843 | 85.175 | 101.220 |
| ATOM | 676 | OE1 | GLU | 68 | 154.693 | 85.730 | 100.495 |
| ATOM | 677 | OE2 | GLU | 68 | 153.381 | 84.119 | 100.743 |
| ATOM | 678 | N | ASN | 69 | 149.711 | 86.252 | 105.036 |
| ATOM | 679 | HN | ASN | 69 | 149.369 | 86.472 | 105.883 |
| ATOM | 680 | CA | ASN | 69 | 149.084 | 86.887 | 103.962 |
| ATOM | 681 | C | ASN | 69 | 148.395 | 88.127 | 104.368 |
| ATOM | 682 | O | ASN | 69 | 148.699 | 89.117 | 103.652 |
| ATOM | 683 | CB | ASN | 69 | 148.284 | 85.932 | 103.035 |
| ATOM | 684 | CG | ASN | 69 | 147.082 | 86.406 | 102.339 |
| ATOM | 685 | OD1 | ASN | 69 | 145.976 | 86.180 | 102.865 |
| ATOM | 686 | ND2 | ASN | 69 | 147.125 | 87.046 | 101.194 |
| ATOM | 687 | HND2 | ASN | 69 | 146.325 | 87.336 | 100.795 |
| ATOM | 688 | HND2 | ASN | 69 | 147.945 | 87.217 | 100.769 |
| ATOM | 689 | N | PHE | 70 | 147.526 | 88.206 | 105.387 |
| ATOM | 690 | HN | PHE | 70 | 147.501 | 87.547 | 106.055 |
| ATOM | 691 | CA | PHE | 70 | 146.569 | 89.228 | 105.544 |
| ATOM | 692 | C | PHE | 70 | 146.632 | 89.940 | 106.840 |
| ATOM | 693 | O | PHE | 70 | 147.156 | 91.065 | 106.791 |
| ATOM | 694 | CB | PHE | 70 | 145.252 | 88.698 | 105.035 |
| ATOM | 695 | CG | PHE | 70 | 144.386 | 89.689 | 104.407 |
| ATOM | 696 | CD1 | PHE | 70 | 143.280 | 90.188 | 105.138 |
| ATOM | 697 | CD2 | PHE | 70 | 144.651 | 90.131 | 103.084 |
| ATOM | 698 | CE1 | PHE | 70 | 142.418 | 91.137 | 104.542 |
| ATOM | 699 | CE2 | PHE | 70 | 143.798 | 91.088 | 102.487 |
| ATOM | 700 | CZ | PHE | 70 | 142.694 | 91.579 | 103.226 |
| ATOM | 701 | N | LEU | 71 | 146.212 | 89.628 | 108.060 |
| ATOM | 702 | HN | LEU | 71 | 146.378 | 90.285 | 108.710 |
| ATOM | 703 | CA | LEU | 71 | 145.565 | 88.489 | 108.541 |
| ATOM | 704 | C | LEU | 71 | 146.377 | 87.305 | 108.854 |
| ATOM | 705 | C | LEU | 71 | 147.034 | 86.694 | 107.961 |
| ATOM | 706 | CB | LEU | 71 | 144.125 | 88.221 | 108.061 |
| ATOM | 707 | CG | LEU | 71 | 143.093 | 88.581 | 109.134 |
| ATOM | 708 | CD1 | LEU | 71 | 141.981 | 89.429 | 108.512 |
| ATOM | 709 | CD2 | LEU | 71 | 142.479 | 87.306 | 109.717 |
| ATOM | 710 | N | PHE | 72 | 146.333 | 86.971 | 110.140 |
| ATOM | 711 | HN | PHE | 72 | 145.821 | 87.541 | 110.685 |
| ATOM | 712 | CA | PHE | 72 | 146.932 | 85.896 | 110.795 |
| ATOM | 713 | C | PHE | 72 | 146.780 | 84.582 | 110.141 |
| ATOM | 714 | O | PHE | 72 | 145.649 | 84.077 | 109.873 |
| ATOM | 715 | CB | PHE | 72 | 146.445 | 85.920 | 112.258 |
| ATOM | 716 | CG | PHE | 72 | 147.494 | 86.159 | 113.257 |
| ATOM | 717 | CD1 | PHE | 72 | 148.218 | 87.382 | 113.299 |
| ATOM | 718 | CD2 | PHE | 72 | 147.771 | 85.134 | 114.197 |
| ATOM | 719 | CE1 | PHE | 72 | 149.223 | 87.574 | 114.279 |
| ATOM | 720 | CE2 | PHE | 72 | 148.776 | 85.318 | 115.177 |
| ATOM | 721 | CZ | PHE | 72 | 149.495 | 86.539 | 11.208 |
| ATOM | 722 | N | LEU | 73 | 147.921 | 83.972 | 109.848 |
| ATOM | 723 | HN | LEU | 73 | 148.717 | 84.370 | 110.150 |
| ATOM | 724 | CA | LEU | 73 | 148.059 | 82.791 | 109.123 |
| ATOM | 725 | C | LEU | 73 | 148.400 | 81.544 | 109.826 |
| ATOM | 726 | O | LEU | 73 | 147.650 | 80.580 | 109.584 |
| ATOM | 727 | CB | LEU | 73 | 148.827 | 82.985 | 107.810 |
| ATOM | 728 | CG | LEU | 73 | 147.883 | 82.573 | 106.679 |
| ATOM | 729 | CD1 | LEU | 73 | 147.543 | 83.802 | 105.841 |
| ATOM | 730 | CD2 | LEU | 73 | 148.527 | 81.482 | 105.825 |
| ATOM | 731 | N | THR | 74 | 149.352 | 81.219 | 110.674 |
| ATOM | 732 | HN | THR | 74 | 149.319 | 80.317 | 110.933 |
| ATOM | 733 | CA | THR | 74 | 150.401 | 81.900 | 111.284 |
| ATOM | 734 | C | THR | 74 | 151.463 | 80.918 | 111.604 |
| ATOM | 735 | O | THR | 74 | 151.431 | 80.644 | 112.832 |
| ATOM | 736 | CB | THR | 74 | 150.691 | 83.386 | 110.992 |
| ATOM | 737 | OG1 | THR | 74 | 151.568 | 83.721 | 109.943 |
| ATOM | 738 | HOG1 | THR | 74 | 152.518 | 83.590 | 110.218 |
| ATOM | 739 | CG2 | THR | 74 | 150.935 | 84.192 | 112.269 |
| ATOM | 740 | N | PRO | 75 | 152.352 | 80.337 | 110.765 |
| ATOM | 741 | CA | PRO | 75 | 153.177 | 79.236 | 111.069 |
| ATOM | 742 | C | PRO | 75 | 153.942 | 79.230 | 112.342 |
| ATOM | 743 | O | PRO | 75 | 154.808 | 80.109 | 112.571 |
| ATOM | 744 | CB | PRO | 75 | 154.043 | 78.927 | 109.841 |
| ATOM | 745 | CG | PRO | 75 | 153.912 | 80.191 | 109.000 |
| ATOM | 746 | CD | PRO | 75 | 152.562 | 80.744 | 109.449 |
| ATOM | 747 | N | ASP | 76 | 153.777 | 78.332 | 113.308 |
| ATOM | 748 | HN | ASP | 76 | 154.317 | 78.422 | 114.072 |
| ATOM | 749 | CA | ASP | 76 | 152.879 | 77.264 | 113.298 |
| ATOM | 750 | C | ASP | 76 | 151.892 | 77.153 | 114.404 |
| ATOM | 751 | C | ASP | 76 | 152.226 | 77.243 | 115.615 |
| ATOM | 752 | CB | ASP | 76 | 153.632 | 75.954 | 113.016 |
| ATOM | 753 | CG | ASP | 76 | 152.785 | 75.113 | 112.176 |
| ATOM | 754 | OD1 | ASP | 76 | 152.210 | 74.123 | 112.674 |
| ATOM | 755 | OD2 | ASP | 76 | 152.636 | 75.398 | 110.967 |
| ATOM | 756 | N | CYS | 77 | 150.592 | 76.950 | 114.225 |
| ATOM | 757 | HN | CYS | 77 | 150.075 | 76.854 | 115.004 |
| ATOM | 758 | CA | CYS | 77 | 149.896 | 76.871 | 113.013 |
| ATOM | 759 | C | CYS | 77 | 149.130 | 78.089 | 112.682 |
| ATOM | 760 | O | CYS | 77 | 149.282 | 78.516 | 111.513 |
| ATOM | 761 | CB | CYS | 77 | 149.013 | 75.611 | 112.961 |
| ATOM | 762 | SG | CYS | 77 | 149.064 | 74.805 | 111.379 |
| ATOM | 763 | N | LYS | 78 | 148.334 | 78.707 | 113.555 |
| ATOM | 764 | HN | LYS | 78 | 148.257 | 78.358 | 114.423 |
| ATOM | 765 | CA | LYS | 78 | 147.578 | 79.851 | 113.363 |
| ATOM | 766 | C | LYS | 78 | 148.088 | 81.062 | 114.048 |
| ATOM | 767 | O | LYS | 78 | 147.870 | 82.112 | 113.403 |
| ATOM | 768 | CB | LYS | 78 | 146.083 | 79.531 | 113.572 |
| ATOM | 769 | CG | LYS | 78 | 145.105 | 80.415 | 112.775 |
| ATOM | 770 | CD | LYS | 78 | 145.103 | 80.116 | 111.269 |
| ATOM | 771 | CE | LYS | 78 | 144.036 | 80.927 | 110.528 |
| ATOM | 772 | NZ | LYS | 78 | 144.491 | 81.430 | 109.229 |
| ATOM | 773 | HNZ | LYS | 78 | 145.049 | 80.741 | 108.728 |
| ATOM | 774 | HNZ | LYS | 78 | 143.669 | 81.647 | 108.667 |
| ATOM | 775 | HNZ | LYS | 78 | 145.000 | 82.299 | 109.394 |
| ATOM | 776 | N | SER | 79 | 148.729 | 81.304 | 115.196 |
| ATOM | 777 | HN | SER | 79 | 148.836 | 82.226 | 115.344 |
| ATOM | 778 | CA | SER | 79 | 149.292 | 80.544 | 116.241 |
| ATOM | 779 | C | SER | 79 | 150.658 | 80.996 | 116.572 |
| ATOM | 780 | O | SER | 79 | 150.797 | 81.466 | 117.732 |
| ATOM | 781 | CB | SER | 79 | 149.158 | 79.022 | 116.458 |
| ATOM | 782 | OG | SER | 79 | 147.823 | 78.550 | 116.591 |
| ATOM | 783 | HOG | SER | 79 | 147.325 | 78.723 | 115.765 |
| ATOM | 784 | N | LEU | 80 | 151.668 | 80.922 | 115.703 |
| ATOM | 785 | CA | LEU | 80 | 152.963 | 81.431 | 115.833 |
| ATOM | 786 | C | LEU | 80 | 153.247 | 82.594 | 114.957 |
| ATOM | 787 | O | LEU | 80 | 152.762 | 83.663 | 115.416 |
| ATOM | 788 | CB | LEU | 80 | 153.999 | 80.296 | 115.934 |
| ATOM | 789 | CG | LEU | 80 | 155.297 | 80.733 | 116.619 |
| ATOM | 790 | CD1 | LEU | 80 | 155.485 | 79.940 | 117.913 |
| ATOM | 791 | CD2 | LEU | 80 | 156.484 | 80.469 | 115.689 |
| ATOM | 792 | N | TRP | 81 | 153.935 | 82.560 | 113.803 |
| ATOM | 793 | HN | TRP | 81 | 154.226 | 81.723 | 113.492 |
| ATOM | 794 | CA | TRP | 81 | 154.290 | 83.629 | 112.961 |
| ATOM | 795 | C | TRP | 81 | 154.985 | 83.254 | 111.709 |
| ATOM | 796 | O | TRP | 81 | 154.324 | 83.406 | 110.650 |
| ATOM | 797 | CB | TRP | 81 | 154.962 | 84.854 | 113.625 |
| ATOM | 798 | CG | TRP | 81 | 154.110 | 86.054 | 113.634 |
| ATOM | 799 | CD1 | TRP | 81 | 153.770 | 86.758 | 114.792 |
| ATOM | 800 | CD2 | TRP | 81 | 153.492 | 86.724 | 112.578 |
| ATOM | 801 | NE1 | TRP | 81 | 152.996 | 87.772 | 114.453 |
| ATOM | 802 | HNE1 | TRP | 81 | 152.634 | 88.391 | 115.059 |
| ATOM | 803 | CE2 | TRP | 81 | 152.799 | 87.796 | 113.157 |
| ATOM | 804 | CE3 | TRP | 81 | 153.466 | 86.500 | 111.179 |
| ATOM | 805 | CZ2 | TRP | 81 | 152.039 | 88.700 | 112.378 |
| ATOM | 806 | CZ3 | TRP | 81 | 152.687 | 87.383 | 110.391 |
| ATOM | 807 | CH2 | TRP | 81 | 151.989 | 88.471 | 110.979 |
| ATOM | 808 | N | ASN | 82 | 156.237 | 82.793 | 111.687 |
| ATOM | 809 | HN | ASN | 82 | 156.556 | 82.385 | 112.473 |
| ATOM | 810 | CA | ASN | 82 | 157.126 | 82.884 | 110.614 |
| ATOM | 811 | C | ASN | 82 | 157.270 | 81.778 | 109.638 |
| ATOM | 812 | O | ASN | 82 | 157.334 | 80.570 | 110.006 |
| ATOM | 813 | CB | ASN | 82 | 158.455 | 83.363 | 111.227 |
| ATOM | 814 | CG | ASN | 82 | 159.240 | 84.228 | 110.346 |
| ATOM | 815 | OD1 | ASN | 82 | 160.047 | 83.703 | 109.548 |
| ATOM | 816 | ND2 | ASN | 82 | 159.123 | 85.532 | 110.380 |
| ATOM | 817 | HND2 | ASN | 82 | 159.677 | 86.063 | 109.838 |
| ATOM | 818 | HND2 | ASN | 82 | 158.489 | 85.940 | 110.941 |
| ATOM | 819 | N | GLY | 83 | 157.333 | 82.163 | 108.368 |
| ATOM | 820 | HN | GLY | 83 | 157.189 | 83.081 | 108.229 |
| ATOM | 821 | CA | GLY | 83 | 157.593 | 81.402 | 107.223 |
| ATOM | 822 | C | GLY | 83 | 157.453 | 82.153 | 105.965 |
| ATOM | 823 | O | GLY | 83 | 156.517 | 81.783 | 105.215 |
| ATOM | 824 | N | ASP | 84 | 158.292 | 83.151 | 105.690 |
| ATOM | 825 | HN | ASP | 84 | 158.966 | 83.290 | 106.330 |
| ATOM | 826 | CA | ASP | 84 | 158.327 | 84.030 | 104.599 |
| ATOM | 827 | C | ASP | 84 | 157.071 | 84.644 | 104.065 |

APPENDIX 1-continued

Kininogen Heavy Chain Domain 2

| ATOM | 828 | O | ASP | 84 | 156.934 | 84.881 | 102.842 |
| ATOM | 829 | CB | ASP | 84 | 159.460 | 83.592 | 103.633 |
| ATOM | 830 | CG | ASP | 84 | 159.065 | 82.772 | 102.480 |
| ATOM | 831 | OD1 | ASP | 84 | 158.775 | 81.563 | 102.610 |
| ATOM | 832 | OD2 | ASP | 84 | 159.000 | 83.272 | 101.332 |
| ATOM | 833 | N | THR | 85 | 155.968 | 85.038 | 104.691 |
| ATOM | 834 | HN | THR | 85 | 155.241 | 85.195 | 104.116 |
| ATOM | 835 | CA | THR | 85 | 155.688 | 85.277 | 106.038 |
| ATOM | 836 | C | THR | 85 | 156.732 | 85.670 | 107.005 |
| ATOM | 837 | O | THR | 85 | 156.919 | 84.955 | 108.026 |
| ATOM | 838 | CB | THR | 85 | 154.321 | 84.728 | 106.495 |
| ATOM | 839 | OG1 | THR | 85 | 153.584 | 85.638 | 107.295 |
| ATOM | 840 | HOG1 | THR | 85 | 152.657 | 85.503 | 107.007 |
| ATOM | 841 | CG2 | THR | 85 | 154.257 | 83.338 | 107.135 |
| ATOM | 842 | N | GLY | 86 | 157.413 | 86.782 | 106.731 |
| ATOM | 843 | HN | GLY | 86 | 157.232 | 87.193 | 105.906 |
| ATOM | 844 | CA | GLY | 86 | 158.352 | 87.401 | 107.565 |
| ATOM | 845 | C | GLY | 86 | 157.747 | 88.498 | 108.336 |
| ATOM | 846 | O | GLY | 86 | 158.299 | 89.617 | 108.225 |
| ATOM | 847 | N | GLU | 87 | 156.669 | 88.255 | 109.081 |
| ATOM | 848 | HN | GLU | 87 | 156.510 | 87.344 | 109.245 |
| ATOM | 849 | CA | GLU | 87 | 155.740 | 89.152 | 109.626 |
| ATOM | 850 | C | GLU | 87 | 155.027 | 89.915 | 108.574 |
| ATOM | 851 | O | GLU | 87 | 155.381 | 91.084 | 108.241 |
| ATOM | 852 | CB | GLU | 87 | 156.205 | 89.875 | 110.909 |
| ATOM | 853 | CG | GLU | 87 | 156.184 | 88.984 | 112.169 |
| ATOM | 854 | CD | GLU | 87 | 157.244 | 87.969 | 112.233 |
| ATOM | 855 | OE1 | GLU | 87 | 158.410 | 88.288 | 112.548 |
| ATOM | 856 | OE2 | GLU | 87 | 157.011 | 86.765 | 111.977 |
| ATOM | 857 | N | CYS | 88 | 154.009 | 89.267 | 108.005 |
| ATOM | 858 | HN | CYS | 88 | 153.741 | 88.467 | 108.420 |
| ATOM | 859 | CA | CYS | 88 | 153.301 | 89.623 | 106.858 |
| ATOM | 860 | C | CYS | 88 | 153.989 | 89.205 | 105.618 |
| ATOM | 861 | O | CYS | 88 | 154.073 | 87.983 | 105.292 |
| ATOM | 862 | CB | CYS | 88 | 151.854 | 89.101 | 106.933 |
| ATOM | 863 | SG | CYS | 88 | 150.624 | 90.247 | 106.369 |
| ATOM | 864 | N | THR | 89 | 154.496 | 90.187 | 104.876 |
| ATOM | 865 | HN | THR | 89 | 154.350 | 91.058 | 105.196 |
| ATOM | 866 | CA | THR | 89 | 155.214 | 90.104 | 103.666 |
| ATOM | 867 | C | THR | 89 | 154.446 | 90.143 | 102.397 |
| ATOM | 868 | O | THR | 89 | 155.036 | 90.711 | 101.431 |
| ATOM | 869 | CB | THR | 89 | 156.604 | 89.413 | 103.603 |
| ATOM | 870 | OG1 | THR | 89 | 156.679 | 88.129 | 104.203 |
| ATOM | 871 | HOG1 | THR | 89 | 155.801 | 87.995 | 104.616 |
| ATOM | 872 | CG2 | THR | 89 | 157.715 | 90.301 | 104.177 |
| ATOM | 873 | N | ASP | 90 | 153.208 | 89.634 | 102.253 |
| ATOM | 874 | HN | ASP | 90 | 152.869 | 89.166 | 102.993 |
| ATOM | 875 | CA | ASP | 90 | 152.377 | 89.739 | 101.120 |
| ATOM | 876 | C | ASP | 90 | 152.208 | 91.108 | 100.589 |
| ATOM | 877 | O | ASP | 90 | 152.789 | 91.327 | 99.489 |
| ATOM | 878 | CB | ASP | 90 | 151.100 | 88.866 | 101.133 |
| ATOM | 879 | CG | ASP | 90 | 150.519 | 88.478 | 99.830 |
| ATOM | 880 | OD1 | ASP | 90 | 149.629 | 87.593 | 99.796 |
| ATOM | 881 | OD2 | ASP | 90 | 150.856 | 88.973 | 98.725 |
| ATOM | 882 | N | ASN | 91 | 151.512 | 92.063 | 101.220 |
| ATOM | 883 | HN | ASN | 91 | 151.051 | 91.792 | 101.992 |
| ATOM | 884 | CA | ASN | 91 | 151.401 | 93.430 | 100.874 |
| ATOM | 885 | C | ASN | 91 | 150.555 | 93.783 | 99.706 |
| ATOM | 886 | O | ASN | 91 | 149.669 | 94.659 | 99.892 |
| ATOM | 887 | CB | ASN | 91 | 152.754 | 94.193 | 100.912 |
| ATOM | 888 | CG | ASN | 91 | 153.345 | 94.302 | 102.252 |
| ATOM | 889 | OD1 | ASN | 91 | 152.205 | 94.369 | 102.889 |
| ATOM | 890 | ND1 | ASN | 91 | 154.009 | 93.310 | 102.800 |
| ATOM | 891 | HND2 | ASN | 91 | 154.181 | 93.321 | 103.723 |
| ATOM | 892 | HND2 | ASN | 91 | 154.307 | 92.578 | 102.293 |
| ATOM | 893 | N | ALA | 92 | 150.759 | 93.176 | 98.534 |
| ATOM | 894 | HN | ALA | 92 | 151.471 | 92.570 | 98.601 |
| ATOM | 895 | CA | ALA | 92 | 150.103 | 93.281 | 97.295 |
| ATOM | 896 | C | ALA | 92 | 149.921 | 94.579 | 96.593 |
| ATOM | 897 | O | ALA | 92 | 150.325 | 94.645 | 95.403 |
| ATOM | 898 | CB | ALA | 92 | 148.849 | 92.387 | 97.308 |
| ATOM | 899 | N | TYR | 93 | 149.348 | 95.601 | 97.224 |
| ATOM | 900 | HN | TYR | 93 | 149.366 | 95.451 | 98.150 |
| ATOM | 901 | CA | TYR | 93 | 148.741 | 96.785 | 96.772 |
| ATOM | 902 | C | TYR | 93 | 149.462 | 97.745 | 94.920 |
| ATOM | 903 | O | TYR | 93 | 149.765 | 97.489 | 94.723 |
| ATOM | 904 | CB | TYR | 93 | 147.264 | 96.603 | 96.350 |
| ATOM | 905 | CG | TYR | 93 | 146.370 | 95.969 | 97.328 |
| ATOM | 906 | CD1 | TYR | 93 | 145.733 | 94.761 | 96.949 |
| ATOM | 907 | CD2 | TYR | 93 | 146.148 | 96.547 | 98.606 |
| ATOM | 908 | CE1 | TYR | 93 | 144.845 | 94.130 | 97.848 |
| ATOM | 909 | CE2 | TYR | 93 | 145.262 | 95.915 | 99.509 |
| ATOM | 910 | CZ | TYR | 93 | 144.614 | 94.721 | 99.112 |
| ATOM | 911 | OH | TYR | 93 | 143.747 | 94.130 | 99.959 |
| ATOM | 912 | HOH | TYR | 93 | 143.565 | 94.525 | 100.837 |
| ATOM | 913 | N | ILE | 94 | 149.756 | 98.919 | 96.482 |
| ATOM | 914 | HN | ILE | 94 | 149.402 | 99.092 | 97.335 |
| ATOM | 915 | CA | ILE | 94 | 150.534 | 99.957 | 95.948 |
| ATOM | 916 | C | ILE | 94 | 149.917 | 101.262 | 96.248 |
| ATOM | 917 | O | ILE | 94 | 150.194 | 101.883 | 97.314 |
| ATOM | 918 | CB | ILE | 94 | 152.085 | 99.896 | 96.085 |
| ATOM | 919 | CG1 | ILE | 94 | 152.748 | 98.993 | 95.032 |
| ATOM | 920 | CG1 | ILE | 94 | 152.668 | 99.576 | 97.476 |
| ATOM | 921 | CD1 | ILE | 94 | 153.137 | 99.769 | 93.767 |
| ATOM | 922 | N | ASP | 95 | 149.066 | 101.712 | 95.332 |
| ATOM | 923 | HN | ASP | 95 | 148.995 | 101.217 | 94.537 |
| ATOM | 924 | CA | ASP | 95 | 148.265 | 102.846 | 95.441 |
| ATOM | 925 | C | ASP | 95 | 146.824 | 102.536 | 95.321 |
| ATOM | 926 | O | ASP | 95 | 146.172 | 102.507 | 96.400 |
| ATOM | 927 | CB | ASP | 95 | 148.825 | 103.952 | 84.526 |
| ATOM | 928 | CG | ASP | 95 | 148.113 | 105.218 | 94.678 |
| ATOM | 929 | OD1 | ASP | 95 | 147.244 | 105.528 | 93.840 |
| ATOM | 930 | OD2 | ASP | 95 | 148.363 | 105.986 | 95.629 |
| ATOM | 931 | N | ILE | 96 | 146.248 | 102.299 | 94.143 |
| ATOM | 932 | CA | ILE | 96 | 144.898 | 102.039 | 93.908 |
| ATOM | 933 | C | ILE | 96 | 144.226 | 103.067 | 93.065 |
| ATOM | 934 | O | ILE | 96 | 143.980 | 102.868 | 91.850 |
| ATOM | 935 | CB | ILE | 96 | 144.612 | 100.523 | 93.754 |
| ATOM | 936 | CG1 | ILE | 96 | 145.057 | 99.868 | 92.434 |
| ATOM | 937 | CG2 | ILE | 96 | 143.159 | 100.158 | 94.090 |
| ATOM | 938 | CD1 | ILE | 96 | 146.334 | 99.039 | 92.623 |
| ATOM | 939 | N | GLN | 97 | 143.829 | 104.258 | 93.505 |
| ATOM | 940 | HN | GLN | 97 | 143.387 | 104.809 | 92.885 |
| ATOM | 941 | CA | GLN | 97 | 143.998 | 104.780 | 94.790 |
| ATOM | 942 | C | GLN | 97 | 143.014 | 104.307 | 95.786 |
| ATOM | 943 | O | GLN | 97 | 141.790 | 104.611 | 95.697 |
| ATOM | 944 | CB | GLN | 97 | 144.161 | 106.313 | 94.726 |
| ATOM | 945 | CG | GLN | 97 | 144.815 | 106.875 | 96.003 |
| ATOM | 946 | CD | GLN | 97 | 145.375 | 108.223 | 85.870 |
| ATOM | 947 | OE1 | GLN | 97 | 144.640 | 109.236 | 95.947 |
| ATOM | 948 | NE2 | GLN | 97 | 146.662 | 108.375 | 95.675 |
| ATOM | 949 | HNE2 | GLN | 97 | 147.035 | 109.234 | 95.596 |
| ATOM | 950 | HNE2 | GLN | 97 | 147.208 | 107.614 | 95.617 |
| ATOM | 951 | N | LEU | 98 | 143.516 | 103.555 | 96.759 |
| ATOM | 952 | HN | LEU | 98 | 144.402 | 103.266 | 96.640 |
| ATOM | 953 | CA | LEU | 98 | 142.909 | 103.129 | 97.944 |
| ATOM | 954 | C | LEU | 98 | 142.159 | 101.854 | 97.878 |
| ATOM | 955 | O | LEU | 98 | 141.190 | 101.697 | 97.099 |
| ATOM | 956 | CB | LEU | 98 | 142.286 | 104.211 | 98.851 |
| ATOM | 957 | CG | LEU | 98 | 143.338 | 104.851 | 99.766 |
| ATOM | 958 | CD1 | LEU | 98 | 143.135 | 106.367 | 99.802 |
| ATOM | 959 | CD2 | LEU | 98 | 143.224 | 104.290 | 101.186 |
| ATOM | 960 | N | ARG | 99 | 142.443 | 100.793 | 98.623 |
| ATOM | 961 | HN | ARG | 99 | 141.935 | 100.017 | 98.465 |
| ATOM | 962 | CA | ARG | 99 | 143.420 | 100.718 | 99.624 |
| ATOM | 963 | C | ARG | 99 | 144.819 | 100.550 | 99.185 |
| ATOM | 964 | O | ARG | 99 | 145.141 | 99.620 | 98.398 |
| ATOM | 965 | CB | ARG | 99 | 143.003 | 99.861 | 100.839 |
| ATOM | 966 | CG | ARG | 99 | 142.869 | 98.341 | 100.628 |
| ATOM | 967 | CD | ARG | 99 | 141.410 | 97.867 | 100.691 |
| ATOM | 968 | NE | ARG | 99 | 140.989 | 97.709 | 102.013 |
| ATOM | 969 | HNE | ARG | 99 | 141.653 | 97.644 | 102.674 |
| ATOM | 970 | CZ | ARG | 99 | 139.772 | 97.636 | 102.530 |
| ATOM | 971 | NH1 | ARG | 99 | 139.803 | 97.517 | 103.830 |
| ATOM | 972 | HNH1 | ARG | 99 | 139.026 | 97.442 | 104.351 |
| ATOM | 973 | HNH1 | ARG | 99 | 140.663 | 97.510 | 104.204 |
| ATOM | 974 | NH2 | ARG | 99 | 138.600 | 97.673 | 101.923 |
| ATOM | 975 | HNH2 | ARG | 99 | 137.807 | 97.616 | 102.426 |
| ATOM | 976 | HNH2 | ARG | 99 | 138.557 | 97.753 | 100.987 |
| ATOM | 977 | N | ILE | 100 | 145.682 | 101.433 | 99.675 |
| ATOM | 978 | HN | ILE | 100 | 145.314 | 102.111 | 100.212 |
| ATOM | 979 | CA | ILE | 100 | 147.072 | 101.483 | 99.498 |
| ATOM | 980 | C | ILE | 100 | 147.792 | 100.222 | 99.817 |
| ATOM | 981 | O | ILE | 100 | 148.526 | 99.739 | 98.920 |

APPENDIX 1-continued

Kininogen Heavy Chain Domain 2

| ATOM | 982 | CB | ILE | 100 | 147.570 | 102.841 | 100.071 |
|------|-----|-----|-----|-----|---------|---------|---------|
| ATOM | 983 | CG1 | ILE | 100 | 147.944 | 103.824 | 98.952 |
| ATOM | 984 | CG2 | ILE | 100 | 148.696 | 102.853 | 101.124 |
| ATOM | 985 | CD1 | ILE | 100 | 146.881 | 104.912 | 98.756 |
| ATOM | 986 | N | ALA | 101 | 147.661 | 99.627 | 101.003 |
| ATOM | 987 | HN | ALA | 101 | 147.091 | 100.056 | 101.614 |
| ATOM | 988 | CA | ALA | 101 | 148.270 | 98.441 | 101.434 |
| ATOM | 989 | C | ALA | 101 | 147.547 | 97.789 | 102.547 |
| ATOM | 990 | O | ALA | 101 | 147.144 | 96.617 | 102.376 |
| ATOM | 991 | CB | ALA | 101 | 149.777 | 98.582 | 101.740 |
| ATOM | 992 | N | SER | 102 | 147.265 | 98.299 | 103.740 |
| ATOM | 993 | HN | SER | 102 | 147.120 | 97.697 | 104.445 |
| ATOM | 994 | CA | SER | 102 | 147.160 | 99.656 | 104.067 |
| ATOM | 995 | C | SER | 102 | 145.802 | 100.170 | 103.755 |
| ATOM | 996 | O | SER | 102 | 145.736 | 101.035 | 102.849 |
| ATOM | 997 | CB | SER | 102 | 147.655 | 100.097 | 105.466 |
| ATOM | 998 | OG | SER | 102 | 148.444 | 99.184 | 106.224 |
| ATOM | 999 | HOG | SER | 102 | 148.024 | 98.299 | 106.179 |
| ATOM | 1000 | N | PHE | 103 | 144.645 | 99.813 | 104.321 |
| ATOM | 1001 | HN | PHE | 103 | 143.868 | 100.265 | 104.043 |
| ATOM | 1002 | CA | PHE | 103 | 144.500 | 98.816 | 105.291 |
| ATOM | 1003 | C | PHE | 103 | 143.856 | 97.568 | 104.840 |
| ATOM | 1004 | O | PHE | 103 | 142.701 | 97.585 | 104.324 |
| ATOM | 1005 | CB | PHE | 103 | 143.928 | 99.360 | 106.615 |
| ATOM | 1006 | CG | PHE | 103 | 144.623 | 98.770 | 107.764 |
| ATOM | 1007 | CD1 | PHE | 103 | 145.691 | 99.485 | 108.365 |
| ATOM | 1008 | CD2 | PHE | 103 | 144.236 | 97.498 | 107.267 |
| ATOM | 1009 | CE1 | PHE | 103 | 146.399 | 98.915 | 109.450 |
| ATOM | 1010 | CE2 | PHE | 103 | 144.943 | 96.924 | 109.351 |
| ATOM | 1011 | CZ | PHE | 103 | 146.021 | 97.637 | 109.931 |
| ATOM | 1012 | N | SER | 104 | 144.549 | 96.448 | 105.009 |
| ATOM | 1013 | HN | SER | 104 | 145.426 | 96.529 | 105.340 |
| ATOM | 1014 | CA | SER | 104 | 144.122 | 95.141 | 104.755 |
| ATOM | 1015 | C | SER | 104 | 144.594 | 94.151 | 105.745 |
| ATOM | 1016 | O | SER | 104 | 143.674 | 93.550 | 106.351 |
| ATOM | 1017 | CB | SER | 104 | 144.242 | 94.709 | 103.282 |
| ATOM | 1018 | OG | SER | 104 | 143.171 | 95.296 | 102.556 |
| ATOM | 1019 | HOG | SER | 104 | 142.941 | 96.103 | 103.062 |
| ATOM | 1020 | N | GLN | 105 | 145.837 | 93.800 | 106.090 |
| ATOM | 1021 | HN | GLN | 105 | 145.895 | 93.152 | 106.766 |
| ATOM | 1022 | CA | GLN | 105 | 147.094 | 94.214 | 105.613 |
| ATOM | 1023 | C | GLN | 105 | 147.734 | 95.447 | 106.130 |
| ATOM | 1024 | O | GLN | 105 | 147.189 | 96.579 | 106.014 |
| ATOM | 1025 | CB | GLN | 105 | 147.418 | 93.961 | 104.123 |
| ATOM | 1026 | CG | GLN | 105 | 147.266 | 92.511 | 103.622 |
| ATOM | 1027 | CD | GLN | 105 | 147.426 | 92.297 | 102.176 |
| ATOM | 1028 | OE1 | GLN | 105 | 146.975 | 93.077 | 101.302 |
| ATOM | 1029 | NE2 | GLN | 105 | 148.065 | 91.232 | 101.764 |
| ATOM | 1030 | HNE2 | GLN | 105 | 148.258 | 91.122 | 100.851 |
| ATOM | 1031 | HNE2 | GLN | 105 | 148.326 | 90.576 | 102.385 |
| ATOM | 1032 | N | ASN | 106 | 148.915 | 95.283 | 106.708 |
| ATOM | 1033 | HN | ASN | 106 | 149.083 | 94.431 | 107.067 |
| ATOM | 1034 | CA | ASN | 106 | 149.953 | 96.206 | 106.849 |
| ATOM | 1035 | C | ASN | 106 | 150.978 | 96.087 | 105.777 |
| ATOM | 1036 | O | ASN | 106 | 151.210 | 97.149 | 105.153 |
| ATOM | 1037 | CB | ASN | 106 | 150.581 | 96.139 | 108.253 |
| ATOM | 1038 | CG | ASN | 106 | 149.859 | 96.820 | 109.329 |
| ATOM | 1039 | OD1 | ASN | 106 | 149.881 | 98.068 | 109.424 |
| ATOM | 1040 | ND2 | ASN | 106 | 149.192 | 96.109 | 110.202 |
| ATOM | 1041 | HND2 | ASN | 106 | 148.711 | 96.531 | 110.889 |
| ATOM | 1042 | HND2 | ASN | 106 | 149.204 | 95.171 | 110.138 |
| ATOM | 1043 | N | CYS | 107 | 151.686 | 95.024 | 105.371 |
| ATOM | 1044 | HN | CYS | 107 | 152.252 | 95.157 | 104.633 |
| ATOM | 1045 | CA | CYS | 107 | 151.657 | 93.734 | 105.912 |
| ATOM | 1046 | C | CYS | 107 | 152.925 | 93.171 | 106.457 |
| ATOM | 1047 | O | CYS | 107 | 153.917 | 92.916 | 105.722 |
| ATOM | 1048 | CB | CYS | 107 | 150.887 | 92.885 | 104.872 |
| ATOM | 1049 | SG | CYS | 107 | 151.233 | 91.155 | 104.681 |
| ATOM | 1050 | N | ASP | 108 | 153.149 | 92.867 | 107.732 |
| ATOM | 1051 | HN | ASP | 108 | 153.907 | 92.337 | 107.894 |
| ATOM | 1052 | CA | ASP | 108 | 152.423 | 93.222 | 108.872 |
| ATOM | 1053 | C | ASP | 108 | 153.368 | 93.438 | 110.005 |
| ATOM | 1054 | O | ASP | 108 | 153.744 | 92.498 | 110.758 |
| ATOM | 1055 | CB | ASP | 108 | 151.290 | 92.211 | 109.165 |
| ATOM | 1056 | CG | ASP | 108 | 149.939 | 92.758 | 109.033 |
| ATOM | 1057 | OD1 | ASP | 108 | 149.319 | 93.200 | 110.023 |
| ATOM | 1058 | OD2 | ASP | 108 | 149.381 | 92.790 | 107.923 |
| ATOM | 1059 | N | ILE | 109 | 153.912 | 94.601 | 110.341 |
| ATOM | 1060 | HN | ILE | 109 | 154.497 | 94.585 | 111.076 |
| ATOM | 1061 | CA | ILE | 109 | 153.720 | 95.851 | 109.727 |
| ATOM | 1062 | C | ILE | 109 | 154.399 | 96.036 | 108.429 |
| ATOM | 1063 | O | ILE | 109 | 153.757 | 96.519 | 107.470 |
| ATOM | 1064 | CB | ILE | 109 | 153.887 | 97.105 | 110.629 |
| ATOM | 1065 | CG1 | ILE | 109 | 155.198 | 97.234 | 111.428 |
| ATOM | 1066 | CG2 | ILE | 109 | 152.681 | 97.347 | 111.549 |
| ATOM | 1067 | CD1 | ILE | 109 | 156.158 | 98.237 | 110.776 |
| ATOM | 1068 | OXT | GLN | 109 | 155.598 | 95.737 | 108.216 |
| CONECT | 1 | 5 | 2 | 3 | 4 | | |
| CONECT | 2 | 1 | | | | | |
| CONECT | 3 | 1 | | | | | |
| CONECT | 4 | 1 | | | | | |
| CONECT | 5 | 1 | 6 | 8 | | | |
| CONECT | 6 | 7 | 5 | 10 | | | |
| CONECT | 7 | 6 | | | | | |
| CONECT | 8 | 9 | 5 | | | | |
| CONECT | 9 | 8 | 30 | | | | |
| CONECT | 10 | 12 | 6 | 11 | | | |
| CONECT | 11 | 10 | | | | | |
| CONECT | 12 | 10 | 13 | 15 | | | |
| CONECT | 13 | 12 | 14 | 19 | | | |
| CONECT | 14 | 13 | | | | | |
| CONECT | 15 | 16 | 12 | | | | |
| CONECT | 16 | 15 | 17 | 18 | | | |
| CONECT | 17 | 16 | | | | | |
| CONECT | 18 | 16 | | | | | |
| CONECT | 19 | 20 | 21 | 13 | | | |
| CONECT | 20 | 19 | | | | | |
| CONECT | 21 | 19 | 22 | | | | |
| CONECT | 22 | 21 | 23 | 24 | | | |
| CONECT | 23 | 22 | | | | | |
| CONECT | 24 | 26 | 22 | 25 | | | |
| CONECT | 25 | 24 | | | | | |
| CONECT | 26 | 24 | 27 | 29 | | | |
| CONECT | 27 | 28 | 26 | 31 | | | |
| CONECT | 28 | 17 | | | | | |
| CONECT | 29 | 30 | 26 | | | | |
| CONECT | 30 | 29 | 9 | | | | |
| CONECT | 31 | 32 | 27 | | | | |
| CONECT | 32 | 31 | 33 | 35 | | | |
| CONECT | 33 | 34 | 32 | 38 | | | |
| CONECT | 34 | 33 | | | | | |
| CONECT | 35 | 36 | 37 | 32 | | | |
| CONECT | 36 | 35 | | | | | |
| CONECT | 37 | 35 | | | | | |
| CONECT | 38 | 33 | 40 | 39 | | | |
| CONECT | 39 | 38 | | | | | |
| CONECT | 40 | 38 | 41 | 43 | | | |
| CONECT | 41 | 42 | 40 | 50 | | | |
| CONECT | 42 | 41 | | | | | |
| CONECT | 43 | 44 | 40 | | | | |
| CONECT | 44 | 43 | 45 | 47 | | | |
| CONECT | 45 | 44 | 48 | 46 | | | |
| CONECT | 46 | 45 | | | | | |
| CONECT | 47 | 44 | 49 | | | | |
| CONECT | 48 | 45 | 49 | | | | |
| CONECT | 49 | 47 | 48 | | | | |
| CONECT | 50 | 51 | 41 | 56 | | | |
| CONECT | 51 | 50 | 52 | 54 | | | |
| CONECT | 52 | 53 | 51 | 57 | | | |
| CONECT | 53 | 52 | | | | | |
| CONECT | 54 | 55 | 51 | | | | |
| CONECT | 55 | 54 | 56 | | | | |
| CONECT | 56 | 55 | 50 | | | | |
| CONECT | 57 | 52 | 59 | 58 | | | |
| CONECT | 58 | 57 | | | | | |
| CONECT | 59 | 57 | 60 | 62 | | | |
| CONECT | 60 | 61 | 59 | 66 | | | |
| CONECT | 61 | 60 | | | | | |
| CONECT | 62 | 63 | 64 | 59 | | | |
| CONECT | 63 | 62 | 65 | | | | |
| CONECT | 64 | 62 | | | | | |
| CONECT | 65 | 63 | | | | | |
| CONECT | 66 | 60 | 68 | 67 | | | |
| CONECT | 67 | 66 | | | | | |

APPENDIX 1-continued

Kininogen Heavy Chain Domain 2

| | | | | |
|---|---|---|---|---|
| CONECT | 68 | 66 | 69 | 71 |
| CONECT | 69 | 70 | 68 | 74 |
| CONECT | 70 | 69 | | |
| CONECT | 71 | 72 | 68 | |
| CONECT | 72 | 71 | 73 | |
| CONECT | 73 | 72 | | |
| CONECT | 74 | 69 | 76 | 75 |
| CONECT | 75 | 74 | | |
| CONECT | 76 | 74 | 77 | 79 |
| CONECT | 77 | 78 | 76 | 83 |
| CONECT | 78 | 77 | | |
| CONECT | 79 | 80 | 82 | 76 |
| CONECT | 80 | 79 | 81 | |
| CONECT | 81 | 80 | | |
| CONECT | 82 | 79 | | |
| CONECT | 83 | 77 | 85 | 84 |
| CONECT | 84 | 83 | | |
| CONECT | 85 | 83 | 86 | 88 |
| CONECT | 86 | 87 | 85 | 95 |
| CONECT | 87 | 86 | | |
| CONECT | 88 | 89 | 85 | |
| CONECT | 89 | 88 | 90 | |
| CONECT | 90 | 89 | 91 | 92 |
| CONECT | 91 | 90 | | |
| CONECT | 92 | 90 | 93 | 94 |
| CONECT | 93 | 92 | | |
| CONECT | 94 | 92 | | |
| CONECT | 95 | 86 | 97 | 95 |
| CONECT | 96 | 95 | | |
| CONECT | 97 | 95 | 98 | 100 |
| CONECT | 98 | 99 | 97 | 103 |
| CONECT | 99 | 98 | | |
| CONECT | 100 | 101 | 97 | |
| CONECT | 101 | 100 | 102 | |
| CONECT | 102 | 101 | | |
| CONECT | 103 | 98 | 104 | 109 |
| CONECT | 104 | 103 | 105 | 107 |
| CONECT | 105 | 106 | 104 | 110 |
| CONECT | 106 | 105 | | |
| CONECT | 107 | 108 | 104 | |
| CONECT | 108 | 107 | 109 | |
| CONECT | 109 | 108 | 103 | |
| CONECT | 110 | 105 | 112 | 111 |
| CONECT | 111 | 110 | | |
| CONECT | 112 | 110 | 113 | 115 |
| CONECT | 113 | 114 | 112 | 119 |
| CONECT | 114 | 113 | | |
| CONECT | 115 | 116 | 112 | |
| CONECT | 116 | 115 | 117 | 118 |
| CONECT | 117 | 116 | | |
| CONECT | 118 | 116 | | |
| CONECT | 119 | 113 | 121 | 120 |
| CONECT | 120 | 119 | | |
| CONECT | 121 | 124 | 119 | 122 |
| CONECT | 122 | 123 | 121 | 128 |
| CONECT | 123 | 122 | | |
| CONECT | 124 | 121 | 125 | |
| CONECT | 125 | 124 | 126 | 127 |
| CONECT | 126 | 125 | | |
| CONECT | 127 | 125 | | |
| CONECT | 128 | 122 | 130 | 129 |
| CONECT | 129 | 128 | | |
| CONECT | 130 | 128 | 131 | 133 |
| CONECT | 131 | 132 | 130 | 138 |
| CONECT | 132 | 131 | | |
| CONECT | 133 | 134 | 130 | |
| CONECT | 134 | 133 | 135 | |
| CONECT | 135 | 134 | 136 | 137 |
| CONECT | 136 | 135 | | |
| CONECT | 137 | 135 | | |
| CONECT | 138 | 131 | 139 | 144 |
| CONECT | 139 | 138 | 140 | 142 |
| CONECT | 140 | 141 | 139 | 145 |
| CONECT | 141 | 140 | | |
| CONECT | 142 | 143 | 139 | |
| CONECT | 143 | 142 | 144 | |
| CONECT | 144 | 143 | 138 | |
| CONECT | 145 | 140 | 147 | 146 |
| CONECT | 146 | 145 | | |
| CONECT | 147 | 145 | 148 | 150 |
| CONECT | 148 | 149 | 147 | 154 |
| CONECT | 149 | 148 | | |
| CONECT | 150 | 151 | 152 | 147 |
| CONECT | 151 | 150 | 153 | |
| CONECT | 152 | 150 | | |
| CONECT | 153 | 151 | | |
| CONECT | 154 | 148 | 156 | 155 |
| CONECT | 155 | 154 | | |
| CONECT | 156 | 159 | 154 | 157 |
| CONECT | 157 | 158 | 156 | 164 |
| CONECT | 158 | 157 | | |
| CONECT | 159 | 156 | 160 | |
| CONECT | 160 | 159 | 161 | 162 |
| CONECT | 161 | 160 | | |
| CONECT | 162 | 160 | | |
| CONECT | 163 | 147 | 165 | 164 |
| CONECT | 164 | 163 | | |
| CONECT | 165 | 163 | 166 | 168 |
| CONECT | 166 | 167 | 165 | 180 |
| CONECT | 167 | 166 | | |
| CONECT | 168 | 169 | 164 | |
| CONECT | 169 | 168 | 170 | |
| CONECT | 170 | 169 | 171 | |
| CONECT | 171 | 170 | 173 | 172 |
| CONECT | 172 | 171 | | |
| CONECT | 173 | 171 | 174 | 177 |
| CONECT | 174 | 173 | 175 | 176 |
| CONECT | 175 | 174 | | |
| CONECT | 176 | 174 | | |
| CONECT | 177 | 173 | 178 | 179 |
| CONECT | 178 | 177 | | |
| CONECT | 179 | 177 | | |
| CONECT | 180 | 166 | 182 | 181 |
| CONECT | 181 | 180 | | |
| CONECT | 182 | 180 | 183 | 185 |
| CONECT | 183 | 184 | 182 | 192 |
| CONECT | 184 | 183 | | |
| CONECT | 185 | 186 | 182 | |
| CONECT | 186 | 185 | 187 | 189 |
| CONECT | 187 | 186 | 190 | 188 |
| CONECT | 188 | 187 | | |
| CONECT | 189 | 186 | 191 | |
| CONECT | 190 | 187 | 191 | |
| CONECT | 191 | 189 | 190 | |
| CONECT | 192 | 183 | 194 | 193 |
| CONECT | 193 | 192 | | |
| CONECT | 194 | 192 | 195 | |
| CONECT | 195 | 196 | 194 | 197 |
| CONECT | 196 | 195 | | |
| CONECT | 197 | 195 | 199 | 198 |
| CONECT | 198 | 197 | | |
| CONECT | 199 | 197 | 200 | 202 |
| CONECT | 200 | 201 | 199 | 206 |
| CONECT | 201 | 200 | | |
| CONECT | 202 | 203 | 204 | 199 |
| CONECT | 203 | 202 | 205 | |
| CONECT | 204 | 202 | | |
| CONECT | 205 | 203 | | |
| CONECT | 206 | 200 | 208 | 207 |
| CONECT | 207 | 206 | | |
| CONECT | 208 | 206 | 209 | 211 |
| CONECT | 209 | 210 | 208 | 218 |
| CONECT | 210 | 209 | | |
| CONECT | 211 | 212 | 208 | |
| CONECT | 212 | 211 | 213 | |
| CONECT | 213 | 212 | 214 | 215 |
| CONECT | 214 | 213 | | |
| CONECT | 215 | 213 | 216 | 217 |
| CONECT | 216 | 215 | | |
| CONECT | 217 | 215 | | |
| CONECT | 218 | 209 | 220 | 219 |
| CONECT | 219 | 218 | | |
| CONECT | 220 | 218 | 221 | 223 |
| CONECT | 221 | 222 | 220 | 232 |

APPENDIX 1-continued

Kininogen Heavy Chain Domain 2

| | | | |
|---|---|---|---|
| CONECT | 222 | 221 | |
| CONECT | 223 | 224 | 220 |
| CONECT | 224 | 223 | 225 | 226 |
| CONECT | 225 | 224 | 227 | |
| CONECT | 226 | 224 | 228 | |
| CONECT | 227 | 225 | 229 | |
| CONECT | 228 | 226 | 229 | |
| CONECT | 229 | 227 | 228 | 230 |
| CONECT | 230 | 229 | 231 | |
| CONECT | 231 | 230 | | |
| CONECT | 232 | 221 | 234 | 233 |
| CONECT | 233 | 232 | | |
| CONECT | 234 | 232 | 235 | 237 |
| CONECT | 235 | 236 | 234 | 244 |
| CONECT | 236 | 235 | | |
| CONECT | 237 | 238 | 234 | |
| CONECT | 238 | 237 | 239 | 240 |
| CONECT | 239 | 238 | 241 | |
| CONECT | 240 | 238 | 242 | |
| CONECT | 241 | 239 | 243 | |
| CONECT | 242 | 240 | 243 | |
| CONECT | 243 | 241 | 242 | |
| CONECT | 244 | 235 | 246 | 245 |
| CONECT | 245 | 244 | | |
| CONECT | 246 | 249 | 244 | 247 |
| CONECT | 247 | 248 | 246 | 255 |
| CONECT | 248 | 247 | | |
| CONECT | 249 | 246 | 250 | |
| CONECT | 250 | 249 | 251 | 252 |
| CONECT | 251 | 250 | | |
| CONECT | 252 | 250 | 254 | 253 |
| CONECT | 253 | 252 | | |
| CONECT | 254 | 252 | | |
| CONECT | 255 | 247 | 257 | 256 |
| CONECT | 256 | 255 | | |
| CONECT | 257 | 255 | 258 | 260 |
| CONECT | 258 | 259 | 257 | 266 |
| CONECT | 259 | 258 | | |
| CONECT | 260 | 261 | 257 | |
| CONECT | 261 | 260 | 262 | 263 |
| CONECT | 262 | 261 | | |
| CONECT | 263 | 261 | 264 | 265 |
| CONECT | 264 | 263 | | |
| CONECT | 265 | 263 | | |
| CONECT | 266 | 258 | 268 | 267 |
| CONECT | 267 | 266 | | |
| CONECT | 268 | 266 | 269 | 271 |
| CONECT | 269 | 270 | 268 | 277 |
| CONECT | 270 | 269 | | |
| CONECT | 271 | 272 | 268 | |
| CONECT | 272 | 271 | 273 | 274 |
| CONECT | 273 | 272 | | |
| CONECT | 274 | 272 | 275 | 276 |
| CONECT | 275 | 274 | | |
| CONECT | 276 | 274 | | |
| CONECT | 277 | 269 | 279 | 278 |
| CONECT | 278 | 277 | | |
| CONECT | 279 | 277 | 280 | 282 |
| CONECT | 280 | 281 | 279 | 286 |
| CONECT | 281 | 280 | | |
| CONECT | 282 | 283 | 285 | 279 |
| CONECT | 283 | 282 | 284 | |
| CONECT | 284 | 283 | | |
| CONECT | 285 | 282 | | |
| CONECT | 286 | 280 | 288 | 287 |
| CONECT | 287 | 286 | | |
| CONECT | 288 | 286 | 289 | 291 |
| CONECT | 289 | 290 | 288 | 298 |
| CONECT | 290 | 289 | | |
| CONECT | 291 | 292 | 288 | |
| CONECT | 292 | 291 | 293 | |
| CONECT | 293 | 292 | 294 | 295 |
| CONECT | 294 | 293 | | |
| CONECT | 295 | 293 | 296 | 297 |
| CONECT | 296 | 295 | | |
| CONECT | 297 | 295 | | |
| CONECT | 298 | 289 | 399 | 299 |
| CONECT | 299 | 298 | | |
| CONECT | 300 | 298 | 301 | 303 |
| CONECT | 301 | 302 | 300 | 310 |
| CONECT | 302 | 301 | | |
| CONECT | 303 | 304 | 300 | |
| CONECT | 304 | 303 | 305 | 307 |
| CONECT | 305 | 304 | 308 | 306 |
| CONECT | 306 | 305 | | |
| CONECT | 307 | 304 | 309 | |
| CONECT | 308 | 305 | 309 | |
| CONECT | 309 | 307 | 308 | |
| CONECT | 310 | 301 | 312 | 311 |
| CONECT | 311 | 310 | | |
| CONECT | 312 | 310 | 313 | 315 |
| CONECT | 313 | 314 | 312 | 318 |
| CONECT | 314 | 313 | | |
| CONECT | 315 | 316 | 312 | |
| CONECT | 316 | 315 | 317 | |
| CONECT | 317 | 316 | | |
| CONECT | 318 | 313 | 320 | 319 |
| CONECT | 319 | 318 | | |
| CONECT | 320 | 318 | 321 | 323 |
| CONECT | 321 | 322 | 320 | 326 |
| CONECT | 322 | 321 | | |
| CONECT | 323 | 324 | 320 | |
| CONECT | 324 | 323 | 325 | |
| CONECT | 325 | 324 | | |
| CONECT | 326 | 321 | 328 | 327 |
| CONECT | 327 | 326 | | |
| CONECT | 328 | 326 | 329 | 331 |
| CONECT | 329 | 330 | 328 | 340 |
| CONECT | 330 | 329 | | |
| CONECT | 331 | 332 | 328 | |
| CONECT | 332 | 331 | 333 | 334 |
| CONECT | 333 | 332 | 335 | |
| CONECT | 334 | 332 | 336 | |
| CONECT | 335 | 333 | 337 | |
| CONECT | 336 | 334 | 337 | |
| CONECT | 337 | 335 | 337 | 338 |
| CONECT | 338 | 337 | 339 | |
| CONECT | 339 | 338 | | |
| CONECT | 340 | 329 | 342 | 341 |
| CONECT | 341 | 340 | | |
| CONECT | 342 | 340 | 343 | 345 |
| CONECT | 343 | 344 | 342 | 352 |
| CONECT | 344 | 343 | | |
| CONECT | 345 | 346 | 342 | |
| CONECT | 346 | 345 | 347 | 348 |
| CONECT | 347 | 346 | 349 | |
| CONECT | 348 | 346 | 350 | |
| CONECT | 349 | 347 | 351 | |
| CONECT | 350 | 348 | 351 | |
| CONECT | 351 | 349 | 350 | |
| CONECT | 352 | 343 | 354 | 353 |
| CONECT | 353 | 352 | | |
| CONECT | 354 | 352 | 355 | 357 |
| CONECT | 355 | 356 | 354 | 361 |
| CONECT | 356 | 355 | | |
| CONECT | 357 | 358 | 354 | |
| CONECT | 358 | 357 | 359 | |
| CONECT | 359 | 358 | 360 | |
| CONECT | 360 | 359 | | |
| CONECT | 361 | 355 | 363 | 362 |
| CONECT | 362 | 361 | | |
| CONECT | 363 | 361 | 364 | 366 |
| CONECT | 364 | 365 | 363 | 370 |
| CONECT | 365 | 364 | | |
| CONECT | 366 | 367 | 363 | |
| CONECT | 367 | 366 | 368 | 369 |
| CONECT | 368 | 367 | | |
| CONECT | 369 | 367 | | |
| CONECT | 370 | 364 | 372 | 371 |
| CONECT | 371 | 370 | | |
| CONECT | 372 | 370 | 373 | 375 |
| CONECT | 373 | 374 | 372 | 381 |
| CONECT | 374 | 373 | | |
| CONECT | 375 | 376 | 372 | |

APPENDIX 1-continued

Kininogen Heavy Chain Domain 2

| | | | | |
|---|---|---|---|---|
| CONECT | 376 | 375 | 377 | 378 |
| CONECT | 377 | 376 | | |
| CONECT | 378 | 376 | 379 | 380 |
| CONECT | 379 | 378 | | |
| CONECT | 380 | 378 | | |
| CONECT | 381 | 373 | 383 | 382 |
| CONECT | 382 | 381 | | |
| CONECT | 383 | 381 | 384 | 386 |
| CONECT | 384 | 385 | 383 | 391 |
| CONECT | 385 | 384 | | |
| CONECT | 386 | 387 | 383 | |
| CONECT | 387 | 386 | 388 | |
| CONECT | 388 | 387 | 389 | 390 |
| CONECT | 389 | 388 | | |
| CONECT | 390 | 399 | | |
| CONECT | 391 | 384 | 393 | 392 |
| CONECT | 392 | 391 | | |
| CONECT | 393 | 396 | 391 | 394 |
| CONECT | 394 | 395 | 393 | 399 |
| CONECT | 395 | 394 | | |
| CONECT | 396 | 393 | 397 | 398 |
| CONECT | 397 | 396 | | |
| CONECT | 398 | 396 | | |
| CONECT | 399 | 394 | 401 | 400 |
| CONECT | 400 | 399 | | |
| CONECT | 401 | 399 | 402 | 404 |
| CONECT | 402 | 403 | 401 | 412 |
| CONECT | 403 | 402 | | |
| CONECT | 404 | 405 | 401 | |
| CONECT | 405 | 404 | 406 | |
| CONECT | 406 | 405 | 407 | |
| CONECT | 407 | 406 | 408 | |
| CONECT | 408 | 407 | 409 | 410 | 411 |
| CONECT | 409 | 408 | | |
| CONECT | 410 | 408 | | |
| CONECT | 411 | 408 | | |
| CONECT | 412 | 402 | 414 | 413 |
| CONECT | 413 | 412 | | |
| CONECT | 414 | 412 | 415 | 417 |
| CONECT | 415 | 416 | 414 | 429 |
| CONECT | 416 | 415 | | |
| CONECT | 417 | 418 | 414 | |
| CONECT | 418 | 417 | 419 | |
| CONECT | 419 | 418 | 420 | |
| CONECT | 420 | 419 | 422 | 421 |
| CONECT | 421 | 420 | | |
| CONECT | 422 | 420 | 423 | 426 |
| CONECT | 423 | 422 | 424 | 425 |
| CONECT | 424 | 423 | | |
| CONECT | 425 | 423 | | |
| CONECT | 426 | 422 | 427 | 428 |
| CONECT | 427 | 426 | | |
| CONECT | 428 | 426 | | |
| CONECT | 429 | 415 | 431 | 430 |
| CONECT | 430 | 429 | | |
| CONECT | 431 | 434 | 429 | 432 |
| CONECT | 432 | 433 | 431 | 435 |
| CONECT | 433 | 432 | | |
| CONECT | 434 | 431 | | |
| CONECT | 435 | 432 | 437 | 436 |
| CONECT | 436 | 435 | | |
| CONECT | 437 | 435 | 438 | 440 |
| CONECT | 438 | 439 | 437 | 447 |
| CONECT | 439 | 438 | | |
| CONECT | 440 | 441 | 437 | |
| CONECT | 441 | 440 | 442 | |
| CONECT | 442 | 441 | 443 | 444 |
| CONECT | 443 | 442 | | |
| CONECT | 444 | 442 | 445 | 446 |
| CONECT | 445 | 444 | | |
| CONECT | 446 | 444 | | |
| CONECT | 447 | 438 | 449 | 448 |
| CONECT | 448 | 447 | | |
| CONECT | 449 | 447 | 450 | 452 |
| CONECT | 450 | 451 | 449 | 464 |
| CONECT | 451 | 450 | | |
| CONECT | 452 | 453 | 449 | |
| CONECT | 453 | 452 | 454 | |
| CONECT | 454 | 453 | 455 | |
| CONECT | 455 | 454 | 457 | 456 |
| CONECT | 456 | 455 | | |
| CONECT | 457 | 455 | 458 | 461 |
| CONECT | 458 | 457 | 459 | 460 |
| CONECT | 459 | 458 | | |
| CONECT | 460 | 458 | | |
| CONECT | 461 | 457 | 462 | 463 |
| CONECT | 462 | 461 | | |
| CONECT | 463 | 461 | | |
| CONECT | 464 | 450 | 466 | 465 |
| CONECT | 465 | 464 | | |
| CONECT | 466 | 469 | 464 | 467 |
| CONECT | 467 | 468 | 466 | 476 |
| CONECT | 468 | 467 | | |
| CONECT | 469 | 466 | 470 | |
| CONECT | 470 | 469 | 471 | |
| CONECT | 471 | 470 | 472 | 473 |
| CONECT | 472 | 471 | | |
| CONECT | 473 | 471 | 475 | 474 |
| CONECT | 474 | 473 | | |
| CONECT | 475 | 473 | | |
| CONECT | 476 | 467 | 478 | 477 |
| CONECT | 477 | 476 | | |
| CONECT | 478 | 476 | 479 | 481 |
| CONECT | 479 | 480 | 478 | 484 |
| CONECT | 480 | 479 | | |
| CONECT | 481 | 482 | 483 | 478 |
| CONECT | 482 | 481 | | |
| CONECT | 483 | 481 | | |
| CONECT | 484 | 479 | 486 | 485 |
| CONECT | 485 | 484 | | |
| CONECT | 486 | 489 | 484 | 487 |
| CONECT | 487 | 488 | 486 | 492 |
| CONECT | 488 | 487 | | |
| CONECT | 489 | 486 | 490 | 491 |
| CONECT | 490 | 489 | | |
| CONECT | 491 | 489 | | |
| CONECT | 492 | 487 | 494 | 493 |
| CONECT | 493 | 492 | | |
| CONECT | 494 | 492 | 495 | 497 |
| CONECT | 495 | 496 | 494 | 498 |
| CONECT | 496 | 495 | | |
| CONECT | 497 | 494 | | |
| CONECT | 498 | 495 | 500 | 499 |
| CONECT | 499 | 498 | | |
| CONECT | 500 | 498 | 501 | |
| CONECT | 501 | 502 | 500 | 503 |
| CONECT | 502 | 501 | | |
| CONECT | 503 | 501 | 505 | 504 |
| CONECT | 504 | 503 | | |
| CONECT | 505 | 503 | 506 | 508 |
| CONECT | 506 | 507 | 505 | 512 |
| CONECT | 507 | 506 | | |
| CONECT | 508 | 509 | 505 | |
| CONECT | 509 | 508 | 510 | 511 |
| CONECT | 510 | 509 | | |
| CONECT | 511 | 509 | | |
| CONECT | 512 | 506 | 514 | 513 |
| CONECT | 513 | 512 | | |
| CONECT | 514 | 512 | 515 | 517 |
| CONECT | 515 | 516 | 514 | 523 |
| CONECT | 516 | 515 | | |
| CONECT | 517 | 518 | 514 | |
| CONECT | 518 | 517 | 519 | 520 |
| CONECT | 519 | 518 | | |
| CONECT | 520 | 518 | 521 | 522 |
| CONECT | 521 | 520 | | |
| CONECT | 522 | 520 | | |
| CONECT | 523 | 515 | 525 | 524 |
| CONECT | 524 | 523 | | |
| CONECT | 525 | 523 | 526 | 528 |
| CONECT | 526 | 527 | 525 | 535 |
| CONECT | 527 | 526 | | |
| CONECT | 528 | 529 | 525 | |
| CONECT | 529 | 528 | 530 | 531 |

APPENDIX 1-continued

Kininogen Heavy Chain Domain 2

| | | | |
|---|---|---|---|
| CONECT 530 | 529 | 532 | |
| CONECT 531 | 529 | 533 | |
| CONECT 532 | 530 | 534 | |
| CONECT 533 | 531 | 534 | |
| CONECT 534 | 532 | 533 | |
| CONECT 535 | 526 | 537 | 536 |
| CONECT 536 | 535 | | |
| CONECT 537 | 535 | 538 | 540 |
| CONECT 538 | 539 | 537 | 552 |
| CONECT 539 | 538 | | |
| CONECT 540 | 541 | 537 | |
| CONECT 541 | 540 | 542 | |
| CONECT 542 | 541 | 543 | |
| CONECT 543 | 542 | 545 | 544 |
| CONECT 544 | 543 | | |
| CONECT 545 | 543 | 546 | 549 |
| CONECT 546 | 545 | 547 | 548 |
| CONECT 547 | 546 | | |
| CONECT 548 | 546 | | |
| CONECT 549 | 545 | 550 | 551 |
| CONECT 550 | 549 | | |
| CONECT 551 | 549 | | |
| CONECT 552 | 538 | 554 | 553 |
| CONECT 553 | 552 | | |
| CONECT 554 | 552 | 555 | 557 |
| CONECT 555 | 556 | 554 | 561 |
| CONECT 556 | 555 | | |
| CONECT 557 | 558 | 559 | 554 |
| CONECT 558 | 557 | 560 | |
| CONECT 559 | 557 | | |
| CONECT 560 | 558 | | |
| CONECT 561 | 555 | 563 | 562 |
| CONECT 562 | 561 | | |
| CONECT 563 | 561 | 564 | 566 |
| CONECT 564 | 565 | 563 | 570 |
| CONECT 565 | 564 | | |
| CONECT 566 | 567 | 569 | 563 |
| CONECT 567 | 566 | 568 | |
| CONECT 568 | 567 | | |
| CONECT 569 | 566 | | |
| CONECT 570 | 564 | 572 | 571 |
| CONECT 571 | 570 | | |
| CONECT 572 | 570 | 573 | 575 |
| CONECT 573 | 574 | 572 | 584 |
| CONECT 574 | 573 | | |
| CONECT 575 | 576 | 572 | |
| CONECT 576 | 575 | 577 | 578 |
| CONECT 577 | 576 | 579 | |
| CONECT 578 | 576 | 580 | |
| CONECT 579 | 577 | 581 | |
| CONECT 580 | 578 | 581 | |
| CONECT 581 | 579 | 580 | 582 |
| CONECT 582 | 581 | 583 | |
| CONECT 583 | 582 | | |
| CONECT 584 | 573 | 586 | 585 |
| CONECT 585 | 584 | | |
| CONECT 586 | 584 | 587 | 589 |
| CONECT 587 | 588 | 586 | 592 |
| CONECT 588 | 587 | | |
| CONECT 589 | 590 | 586 | |
| CONECT 590 | 589 | 591 | |
| CONECT 591 | 590 | | |
| CONECT 592 | 587 | 594 | 593 |
| CONECT 593 | 592 | | |
| CONECT 594 | 592 | 595 | 597 |
| CONECT 595 | 596 | 594 | 601 |
| CONECT 596 | 595 | | |
| CONECT 597 | 598 | 599 | 594 |
| CONECT 598 | 597 | 600 | |
| CONECT 599 | 597 | | |
| CONECT 600 | 598 | | |
| CONECT 601 | 595 | 603 | 602 |
| CONECT 602 | 601 | | |
| CONECT 603 | 601 | 604 | 606 |
| CONECT 604 | 605 | 603 | 609 |
| CONECT 605 | 604 | | |
| CONECT 606 | 607 | 608 | 603 |
| CONECT 607 | 606 | | |
| CONECT 608 | 606 | | |
| CONECT 609 | 604 | 611 | 610 |
| CONECT 610 | 609 | | |
| CONECT 611 | 609 | 612 | 614 |
| CONECT 612 | 613 | 611 | 621 |
| CONECT 613 | 612 | | |
| CONECT 614 | 615 | 611 | |
| CONECT 615 | 614 | 616 | |
| CONECT 616 | 615 | 617 | 618 |
| CONECT 617 | 616 | | |
| CONECT 618 | 616 | 619 | 620 |
| CONECT 619 | 618 | | |
| CONECT 620 | 618 | | |
| CONECT 621 | 612 | 623 | 622 |
| CONECT 622 | 621 | | |
| CONECT 623 | 626 | 621 | 624 |
| CONECT 624 | 625 | 623 | 630 |
| CONECT 625 | 624 | | |
| CONECT 626 | 623 | 627 | 629 |
| CONECT 627 | 626 | 628 | |
| CONECT 628 | 627 | | |
| CONECT 629 | 626 | | |
| CONECT 630 | 624 | 632 | 631 |
| CONECT 631 | 630 | | |
| CONECT 632 | 630 | 632 | 635 |
| CONECT 633 | 634 | 632 | 641 |
| CONECT 634 | 633 | | |
| CONECT 635 | 636 | 632 | |
| CONECT 636 | 635 | 637 | 638 |
| CONECT 637 | 636 | | |
| CONECT 638 | 636 | 639 | 640 |
| CONECT 639 | 638 | | |
| CONECT 640 | 638 | | |
| CONECT 641 | 633 | 643 | 642 |
| CONECT 642 | 641 | | |
| CONECT 643 | 646 | 641 | 644 |
| CONECT 644 | 645 | 643 | 648 |
| CONECT 645 | 644 | | |
| CONECT 646 | 643 | 647 | |
| CONECT 647 | 646 | 762 | |
| CONECT 648 | 649 | 644 | |
| CONECT 649 | 648 | 650 | 652 |
| CONECT 650 | 651 | 649 | 655 |
| CONECT 651 | 650 | | |
| CONECT 652 | 653 | 649 | |
| CONECT 653 | 652 | 654 | |
| CONECT 654 | 653 | | |
| CONECT 655 | 650 | 657 | 656 |
| CONECT 656 | 655 | | |
| CONECT 657 | 660 | 655 | 658 |
| CONECT 658 | 659 | 657 | 668 |
| CONECT 659 | 658 | | |
| CONECT 660 | 657 | 661 | |
| CONECT 661 | 660 | 662 | |
| CONECT 662 | 661 | 663 | |
| CONECT 663 | 662 | 664 | |
| CONECT 664 | 663 | 667 | 666 | 665 |
| CONECT 665 | 664 | | |
| CONECT 666 | 664 | | |
| CONECT 667 | 664 | | |
| CONECT 668 | 658 | 670 | 669 |
| CONECT 669 | 668 | | |
| CONECT 670 | 668 | 671 | 673 |
| CONECT 671 | 672 | 670 | 678 |
| CONECT 672 | 671 | | |
| CONECT 673 | 674 | 670 | |
| CONECT 674 | 673 | 675 | |
| CONECT 675 | 674 | 676 | 677 |
| CONECT 676 | 675 | | |
| CONECT 677 | 675 | | |
| CONECT 678 | 671 | 680 | 679 |
| CONECT 679 | 678 | | |
| CONECT 680 | 678 | 681 | 683 |
| CONECT 681 | 682 | 680 | 689 |
| CONECT 682 | 681 | | |
| CONECT 683 | 684 | 680 | |

APPENDIX 1-continued

Kininogen Heavy Chain Domain 2

| | | | | |
|---|---|---|---|---|
| CONECT | 684 | 683 | 685 | 686 |
| CONECT | 685 | 684 | | |
| CONECT | 686 | 684 | 687 | 688 |
| CONECT | 687 | 686 | | |
| CONECT | 688 | 686 | | |
| CONECT | 689 | 681 | 691 | 690 |
| CONECT | 690 | 689 | | |
| CONECT | 691 | 689 | 692 | 694 |
| CONECT | 692 | 693 | 691 | 701 |
| CONECT | 693 | 692 | | |
| CONECT | 694 | 695 | 691 | |
| CONECT | 695 | 694 | 696 | 697 |
| CONECT | 696 | 695 | 698 | |
| CONECT | 697 | 695 | 699 | |
| CONECT | 698 | 696 | 700 | |
| CONECT | 699 | 697 | 700 | |
| CONECT | 700 | 698 | 699 | |
| CONECT | 701 | 692 | 703 | 702 |
| CONECT | 702 | 701 | | |
| CONECT | 703 | 701 | 704 | 706 |
| CONECT | 704 | 705 | 703 | 710 |
| CONECT | 705 | 704 | | |
| CONECT | 706 | 707 | 703 | |
| CONECT | 707 | 706 | 708 | 709 |
| CONECT | 708 | 707 | | |
| CONECT | 709 | 707 | | |
| CONECT | 710 | 712 | 704 | 711 |
| CONECT | 711 | 710 | | |
| CONECT | 712 | 710 | 713 | 715 |
| CONECT | 713 | 714 | 712 | 722 |
| CONECT | 714 | 713 | | |
| CONECT | 715 | 716 | 712 | |
| CONECT | 716 | 715 | 717 | 718 |
| CONECT | 717 | 716 | 719 | |
| CONECT | 718 | 716 | 720 | |
| CONECT | 719 | 717 | 721 | |
| CONECT | 720 | 718 | 721 | |
| CONECT | 721 | 719 | 720 | |
| CONECT | 722 | 713 | 724 | 723 |
| CONECT | 723 | 722 | | |
| CONECT | 724 | 722 | 725 | 727 |
| CONECT | 725 | 726 | 724 | 731 |
| CONECT | 726 | 725 | | |
| CONECT | 727 | 728 | 724 | |
| CONECT | 728 | 727 | 729 | 730 |
| CONECT | 729 | 728 | | |
| CONECT | 730 | 728 | | |
| CONECT | 731 | 725 | 733 | 732 |
| CONECT | 732 | 731 | | |
| CONECT | 733 | 731 | 734 | 736 |
| CONECT | 734 | 735 | 733 | 740 |
| CONECT | 735 | 734 | | |
| CONECT | 736 | 737 | 739 | 733 |
| CONECT | 737 | 736 | 738 | |
| CONECT | 738 | 737 | | |
| CONECT | 739 | 736 | | |
| CONECT | 740 | 734 | 741 | 746 |
| CONECT | 741 | 740 | 742 | 744 |
| CONECT | 742 | 743 | 741 | 747 |
| CONECT | 743 | 742 | | |
| CONECT | 744 | 745 | 741 | |
| CONECT | 745 | 744 | 746 | |
| CONECT | 746 | 745 | 740 | |
| CONECT | 747 | 743 | 749 | 748 |
| CONECT | 748 | 747 | | |
| CONECT | 749 | 747 | 750 | 752 |
| CONECT | 750 | 751 | 749 | 756 |
| CONECT | 751 | 750 | | |
| CONECT | 752 | 753 | 749 | |
| CONECT | 753 | 752 | 754 | 755 |
| CONECT | 754 | 753 | | |
| CONECT | 755 | 753 | | |
| CONECT | 756 | 750 | 758 | 757 |
| CONECT | 757 | 756 | | |
| CONECT | 758 | 756 | 759 | 761 |
| CONECT | 759 | 760 | 758 | 763 |
| CONECT | 760 | 759 | | |

APPENDIX 1-continued

Kininogen Heavy Chain Domain 2

| | | | | |
|---|---|---|---|---|
| CONECT | 761 | 762 | 758 | |
| CONECT | 762 | 761 | 647 | |
| CONECT | 763 | 759 | 765 | 764 |
| CONECT | 764 | 763 | | |
| CONECT | 765 | 763 | 766 | 768 |
| CONECT | 766 | 767 | 765 | 776 |
| CONECT | 767 | 766 | | |
| CONECT | 768 | 769 | 765 | |
| CONECT | 769 | 768 | 770 | |
| CONECT | 770 | 769 | 771 | |
| CONECT | 771 | 770 | 772 | |
| CONECT | 772 | 771 | 773 | 774 | 775 |
| CONECT | 773 | 772 | | |
| CONECT | 774 | 772 | | |
| CONECT | 775 | 772 | | |
| CONECT | 776 | 766 | 778 | 777 |
| CONECT | 777 | 776 | | |
| CONECT | 778 | 776 | 779 | 781 |
| CONECT | 779 | 780 | 778 | 784 |
| CONECT | 780 | 779 | | |
| CONECT | 781 | 782 | 778 | |
| CONECT | 782 | 781 | 783 | |
| CONECT | 783 | 782 | | |
| CONECT | 784 | 785 | 779 | |
| CONECT | 785 | 784 | 786 | 788 |
| CONECT | 786 | 787 | 785 | 792 |
| CONECT | 787 | 786 | | |
| CONECT | 788 | 789 | 785 | |
| CONECT | 789 | 788 | 790 | 791 |
| CONECT | 790 | 789 | | |
| CONECT | 791 | 789 | | |
| CONECT | 792 | 786 | 794 | 793 |
| CONECT | 793 | 792 | | |
| CONECT | 794 | 792 | 795 | 797 |
| CONECT | 795 | 796 | 794 | 808 |
| CONECT | 796 | 795 | | |
| CONECT | 797 | 798 | 794 | |
| CONECT | 798 | 797 | 799 | 800 |
| CONECT | 799 | 798 | 801 | |
| CONECT | 800 | 798 | 803 | 804 |
| CONECT | 801 | 799 | 803 | 802 |
| CONECT | 802 | 801 | | |
| CONECT | 803 | 800 | 801 | 805 |
| CONECT | 804 | 800 | 806 | |
| CONECT | 805 | 803 | 807 | |
| CONECT | 806 | 804 | 807 | |
| CONECT | 807 | 805 | 806 | |
| CONECT | 808 | 795 | 810 | 809 |
| CONECT | 809 | 808 | | |
| CONECT | 810 | 808 | 811 | 813 |
| CONECT | 811 | 812 | 810 | 819 |
| CONECT | 812 | 811 | | |
| CONECT | 813 | 814 | 810 | |
| CONECT | 814 | 813 | 815 | 816 |
| CONECT | 815 | 814 | | |
| CONECT | 816 | 814 | 817 | 818 |
| CONECT | 817 | 816 | | |
| CONECT | 818 | 816 | | |
| CONECT | 819 | 811 | 821 | 820 |
| CONECT | 820 | 819 | | |
| CONECT | 821 | 819 | 822 | |
| CONECT | 822 | 823 | 821 | 8924 |
| CONECT | 823 | 822 | | |
| CONECT | 824 | 822 | 826 | 825 |
| CONECT | 825 | 824 | | |
| CONECT | 826 | 824 | 827 | 829 |
| CONECT | 827 | 828 | 826 | 833 |
| CONECT | 828 | 827 | | |
| CONECT | 829 | 830 | 826 | |
| CONECT | 830 | 829 | 831 | 832 |
| CONECT | 831 | 830 | | |
| CONECT | 832 | 830 | | |
| CONECT | 833 | 827 | 835 | 834 |
| CONECT | 834 | 833 | | |
| CONECT | 835 | 833 | 836 | 838 |
| CONECT | 836 | 837 | 835 | 842 |
| CONECT | 837 | 836 | | |

APPENDIX 1-continued

Kininogen Heavy Chain Domain 2

| CONECT | 838 | 839 | 841 | 835 |
| --- | --- | --- | --- | --- |
| CONECT | 839 | 838 | 840 | |
| CONECT | 840 | 839 | | |
| CONECT | 841 | 838 | | |
| CONECT | 842 | 836 | 844 | 843 |
| CONECT | 843 | 842 | | |
| CONECT | 844 | 842 | 845 | |
| CONECT | 845 | 846 | 844 | 847 |
| CONECT | 846 | 845 | | |
| CONECT | 847 | 845 | 849 | 848 |
| CONECT | 848 | 847 | | |
| CONECT | 849 | 847 | 850 | 852 |
| CONECT | 850 | 851 | 849 | 857 |
| CONECT | 851 | 850 | | |
| CONECT | 852 | 853 | 849 | |
| CONECT | 853 | 852 | 854 | |
| CONECT | 854 | 853 | 855 | 856 |
| CONECT | 855 | 854 | | |
| CONECT | 856 | 854 | | |
| CONECT | 857 | 850 | 859 | 858 |
| CONECT | 858 | 857 | | |
| CONECT | 859 | 862 | 857 | 860 |
| CONECT | 860 | 861 | 859 | 864 |
| CONECT | 861 | 860 | | |
| CONECT | 862 | 859 | 863 | |
| CONECT | 863 | 862 | 1049 | |
| CONECT | 864 | 860 | 866 | 865 |
| CONECT | 865 | 864 | | |
| CONECT | 866 | 864 | 867 | 869 |
| CONECT | 867 | 868 | 8766 | 873 |
| CONECT | 868 | 867 | | |
| CONECT | 869 | 870 | 872 | 866 |
| CONECT | 870 | 869 | 871 | |
| CONECT | 871 | 870 | | |
| CONECT | 872 | 869 | | |
| CONECT | 873 | 867 | 875 | 874 |
| CONECT | 874 | 873 | | |
| CONECT | 875 | 873 | 876 | 878 |
| CONECT | 876 | 877 | 875 | 882 |
| CONECT | 877 | 876 | | |
| CONECT | 878 | 879 | 875 | |
| CONECT | 879 | 878 | 880 | 881 |
| CONECT | 880 | 879 | | |
| CONECT | 881 | 879 | | |
| CONECT | 882 | 876 | 884 | 883 |
| CONECT | 883 | 882 | | |
| CONECT | 884 | 882 | 885 | 887 |
| CONECT | 885 | 886 | 884 | 893 |
| CONECT | 886 | 885 | | |
| CONECT | 887 | 888 | 884 | |
| CONECT | 888 | 887 | 889 | 890 |
| CONECT | 889 | 888 | | |
| CONECT | 890 | 888 | 891 | 892 |
| CONECT | 891 | 890 | | |
| CONECT | 892 | 890 | | |
| CONECT | 893 | 885 | 895 | 894 |
| CONECT | 894 | 893 | | |
| CONECT | 895 | 893 | 896 | 898 |
| CONECT | 896 | 897 | 895 | 899 |
| CONECT | 897 | 896 | | |
| CONECT | 898 | 895 | | |
| CONECT | 899 | 896 | 901 | 900 |
| CONECT | 900 | 899 | | |
| CONECT | 901 | 904 | 899 | 902 |
| CONECT | 902 | 903 | 901 | 913 |
| CONECT | 903 | 902 | | |
| CONECT | 904 | 901 | 905 | |
| CONECT | 905 | 904 | 906 | 907 |
| CONECT | 906 | 905 | 908 | |
| CONECT | 907 | 905 | 909 | |
| CONECT | 908 | 906 | 910 | |
| CONECT | 909 | 907 | 910 | |
| CONECT | 910 | 908 | 909 | 911 |
| CONECT | 911 | 910 | 912 | |
| CONECT | 912 | 911 | | |
| CONECT | 913 | 902 | 915 | 914 |
| CONECT | 914 | 913 | | |
| CONECT | 915 | 913 | 916 | 918 |
| CONECT | 916 | 917 | 915 | 922 |
| CONECT | 917 | 916 | | |
| CONECT | 918 | 919 | 920 | 915 |
| CONECT | 919 | 918 | 921 | |
| CONECT | 920 | 918 | | |
| CONECT | 921 | 919 | | |
| CONECT | 922 | 916 | 924 | 923 |
| CONECT | 923 | 922 | | |
| CONECT | 924 | 922 | 925 | 927 |
| CONECT | 925 | 926 | 924 | 931 |
| CONECT | 926 | 925 | | |
| CONECT | 927 | 928 | 924 | |
| CONECT | 928 | 927 | 929 | 930 |
| CONECT | 929 | 928 | | |
| CONECT | 930 | 928 | | |
| CONECT | 931 | 932 | 925 | |
| CONECT | 932 | 931 | 933 | 935 |
| CONECT | 933 | 934 | 932 | 939 |
| CONECT | 934 | 933 | | |
| CONECT | 935 | 936 | 937 | 932 |
| CONECT | 936 | 935 | 938 | |
| CONECT | 937 | 935 | | |
| CONECT | 938 | 936 | | |
| CONECT | 939 | 933 | 941 | 940 |
| CONECT | 940 | 939 | | |
| CONECT | 941 | 939 | 942 | 944 |
| CONECT | 942 | 943 | 941 | 951 |
| CONECT | 943 | 942 | | |
| CONECT | 944 | 945 | 941 | |
| CONECT | 945 | 944 | 946 | |
| CONECT | 946 | 945 | 947 | 948 |
| CONECT | 947 | 946 | | |
| CONECT | 948 | 946 | 949 | 950 |
| CONECT | 949 | 948 | | |
| CONECT | 950 | 948 | | |
| CONECT | 951 | 942 | 953 | 952 |
| CONECT | 952 | 951 | | |
| CONECT | 953 | 951 | 954 | 956 |
| CONECT | 954 | 955 | 953 | 960 |
| CONECT | 955 | 954 | | |
| CONECT | 956 | 957 | 953 | |
| CONECT | 957 | 956 | 958 | 959 |
| CONECT | 958 | 957 | | |
| CONECT | 959 | 957 | | |
| CONECT | 960 | 954 | 962 | 961 |
| CONECT | 961 | 960 | | |
| CONECT | 962 | 960 | 963 | 965 |
| CONECT | 963 | 964 | 962 | 977 |
| CONECT | 964 | 963 | | |
| CONECT | 965 | 966 | 962 | |
| CONECT | 966 | 965 | 967 | |
| CONECT | 967 | 966 | 968 | |
| CONECT | 968 | 967 | 970 | 696 |
| CONECT | 969 | 968 | | |
| CONECT | 970 | 968 | 971 | 974 |
| CONECT | 971 | 970 | 972 | 973 |
| CONECT | 972 | 971 | | |
| CONECT | 973 | 971 | | |
| CONECT | 974 | 970 | 975 | 976 |
| CONECT | 975 | 974 | | |
| CONECT | 976 | 974 | | |
| CONECT | 977 | 963 | 979 | 978 |
| CONECT | 978 | 977 | | |
| CONECT | 979 | 977 | 980 | 982 |
| CONECT | 980 | 981 | 979 | 986 |
| CONECT | 981 | 980 | | |
| CONECT | 982 | 983 | 984 | 979 |
| CONECT | 983 | 982 | 985 | |
| CONECT | 984 | 982 | | |
| CONECT | 985 | 983 | | |
| CONECT | 986 | 980 | 988 | 987 |
| CONECT | 987 | 986 | | |
| CONECT | 988 | 986 | 989 | 991 |
| CONECT | 989 | 990 | 988 | 992 |
| CONECT | 990 | 989 | | |
| CONECT | 991 | 988 | | |

APPENDIX 1-continued

Kininogen Heavy Chain Domain 2

| CONECT | 992 | 989 | 994 | 993 |
|--------|-----|-----|-----|------|
| CONECT | 993 | 992 | | |
| CONECT | 994 | 992 | 995 | 997 |
| CONECT | 995 | 996 | 994 | 1000 |
| CONECT | 996 | 995 | | |
| CONECT | 997 | 998 | 994 | |
| CONECT | 998 | 997 | 999 | |
| CONECT | 999 | 998 | | |
| CONECT | 1000 | 995 | 1002 | 1001 |
| CONECT | 1001 | 1000 | | |
| CONECT | 1002 | 1000 | 1003 | 1005 |
| CONECT | 1003 | 1004 | 1002 | 1012 |
| CONECT | 1004 | 1003 | | |
| CONECT | 1005 | 1006 | 1002 | |
| CONECT | 1006 | 1005 | 1007 | 1008 |
| CONECT | 1007 | 1006 | 1009 | |
| CONECT | 1008 | 1006 | 1010 | |
| CONECT | 1009 | 1007 | 1011 | |
| CONECT | 1010 | 1008 | 1011 | |
| CONECT | 1011 | 1009 | 1010 | |
| CONECT | 1012 | 1003 | 1014 | 1013 |
| CONECT | 1013 | 1012 | | |
| CONECT | 1014 | 1012 | 1015 | 1017 |
| CONECT | 1015 | 1016 | 1014 | 1020 |
| CONECT | 1016 | 1015 | | |
| CONECT | 1017 | 1018 | 1014 | |
| CONECT | 1018 | 1017 | 1019 | |
| CONECT | 1019 | 1018 | | |
| CONECT | 1020 | 1015 | 1022 | 1021 |
| CONECT | 1021 | 1020 | | |
| CONECT | 1022 | 1020 | 1023 | 1025 |
| CONECT | 1023 | 1024 | 1022 | 1032 |
| CONECT | 1024 | 1023 | | |
| CONECT | 1025 | 1026 | 1022 | |
| CONECT | 1026 | 1025 | 1027 | |
| CONECT | 1027 | 1026 | 1028 | 1029 |
| CONECT | 1028 | 1027 | | |
| CONECT | 1029 | 1027 | 1030 | 1031 |
| CONECT | 1030 | 1029 | | |
| CONECT | 1031 | 1029 | | |
| CONECT | 1032 | 1023 | 1034 | 1033 |
| CONECT | 1033 | 1032 | | |
| CONECT | 1034 | 1032 | 1035 | 1037 |
| CONECT | 1035 | 1036 | 1034 | 1043 |
| CONECT | 1036 | 1035 | | |
| CONECT | 1037 | 1038 | 1034 | |
| CONECT | 1038 | 1037 | 1039 | 1040 |
| CONECT | 1039 | 1038 | | |
| CONECT | 1040 | 1038 | 1041 | 1042 |
| CONECT | 1041 | 1040 | | |
| CONECT | 1042 | 1040 | | |
| CONECT | 1043 | 1035 | 1045 | 1044 |
| CONECT | 1044 | 1043 | | |
| CONECT | 1045 | 1043 | 1046 | 1048 |
| CONECT | 1046 | 1047 | 1045 | 1050 |
| CONECT | 1047 | 1046 | | |
| CONECT | 1048 | 1049 | 1045 | |
| CONECT | 1049 | 1048 | 863 | |
| CONECT | 1050 | 1046 | 1052 | 1051 |
| CONECT | 1051 | 1050 | | |
| CONECT | 1052 | 1050 | 1053 | 1055 |
| CONECT | 1053 | 1054 | 1052 | 1059 |
| CONECT | 1054 | 1053 | | |
| CONECT | 1055 | 1056 | 1052 | |
| CONECT | 1056 | 1055 | 1057 | 1058 |
| CONECT | 1057 | 1056 | | |
| CONECT | 1058 | 1056 | | |
| CONECT | 1059 | 1053 | 1061 | 1060 |
| CONECT | 1060 | 1059 | | |
| CONECT | 1061 | 1059 | 1062 | 1064 |
| CONECT | 1062 | 1063 | 1068 | 1061 |
| CONECT | 1063 | 1062 | | |
| CONECT | 1064 | 1065 | 1066 | 1061 |
| CONECT | 1065 | 1064 | 1067 | |
| CONECT | 1066 | 1064 | | |
| CONECT | 1067 | 1065 | | |
| CONECT | 1068 | 1062 | | |

---

We claim:

1. A method of designing a peptide analog to domain 2 of human kininogen heavy chain comprising:

determining the distance between two parts of a molecular model of the kininogen heavy chain domain 2, at conformational equilibrium;

modifying the primary structure of the domain to restrict the distance between said two parts to the determined distance; and synthesizing a peptide comprising said modified primary structure.

2. The method of claim 1 wherein the step of modifying the primary structure comprises introducing one or more cysteine residues to form an intramolecular disulfide bond.

3. The method of claim 1 wherein the step of modifying the primary structure comprises introducing an amino acid selected from the group consisting of lysine, glutamic acid or aspartic acid into the domain.

4. The method of claim 1 wherein the step of modifying comprises reacting side chains of a lysine and a glutamic or aspartic acid residue to form an amide bond internally cross-linking the domain.

5. The method of claim 1 wherein the step of modifying comprises introducing a toluene-2,4-diisocyanate to internally cross-link two free amino groups of the domain.

6. A method according to claim 1 wherein the molecular model comprises the set of coordinates and connect statement of Appendix 1.

7. A method of producing a peptide having a restricted conformation, comprising:

providing a peptide having an amino acid sequence which is substantially homologous to a portion of domain 2 of the human kininogen heavy chain;

determining the conformational equilibrium of that portion of domain 2; and introducing a covalent modification into the peptide to restrict a distance between two parts of the peptide to a distance between two corresponding parts of the peptide in the equilibrium conformation determined.

8. A method according to claim 7 wherein the modification comprises a cysteine residue capable of forming an intramolecular cysteine-cysteine disulfide bond.

9. The method according to claim 7 wherein the modification comprises a molecule of toluene 2,4-diisocyanate linking two amino groups.

10. The method according to claim 7 wherein the modification comprises an amide bond cross-linking a lysine residue and a glutamic or aspartic acid residue.

11. A method according to claim 7, wherein the peptide having an amino acid sequence which is substantially homologous to a portion of domain 2 of the human kininogen heavy chain consists essentially of an amino acid sequence from about five to about fifty amino acids wherein said sequence has greater than 90% sequence identity with a segment of amino acids 124–232 of the native mature human kininogen heavy chain, and wherein the conformational equilibrium is determined from an equilibrium conformation model.

12. A method according to claim 11 wherein the equilibrium conformation model comprises the set of coordinates and connect statement of Appendix 1.

13. A method of inhibiting the activity of calpain comprising contacting calpain with:

(a) a synthetic peptide consisting essentially of an amino acid sequence of up to about 50 amino acids wherein the amino acid sequence comprises SEQ ID NO:1, said peptide having an artificially introduced restricted conformation, or (b) a pharmaceutically acceptable salt of (a);

wherein said peptide or salt has the ability to inhibit the activity of calpain.

14. The method of claim 13 wherein the peptide or salt is attached to an additional linker sequence wherein the additional linker sequence is from about 1 to 100 amino acids.

15. The method of claim 14 wherein the linker sequence is further linked to a detectable label, solid matrix, or carrier.

16. The method of claim 13 wherein the restricted conformation is determined from an equilibrium conformation model which comprises the set of coordinates and connect statement of Appendix 1.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 20 amino acids
        ( B ) TYPE: amino acid
        ( C ) TOPOLOGY: linear ( x i ) SEQUENCE DESCRIPTION: SEQ ID NO:1:

Cys Thr Asp Asn Ala Tyr Ile Asp Ile Gln
                          5                        10

Leu Arg Ile Ala Ser Phe Ser Gln Asn Cys
                          15                        20

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( C ) TOPOLOGY: linear ( x i ) SEQUENCE DESCRIPTION: SEQ ID NO:2:

Gln Val Val Ala Gly
5